(12) United States Patent
Altman et al.

(10) Patent No.: US 9,932,350 B2
(45) Date of Patent: Apr. 3, 2018

(54) INHIBITORS OF IRAK4 ACTIVITY

(71) Applicants: MERCK SHARP & DOHME CORP., Rahway, NJ (US); Craig R. Gibeau, Holliston, MA (US); Solomon D. Kattar, Wakefield, MA (US); Charles A. Lesburg, Newton, MA (US); Jongwon Lim, Lexington, MA (US); John K. F. Maclean, Ayrshire (GB); Umar F. Mansoor, Hopkinton, MA (US); Alan B. Northrup, Reading, MA (US); John M. Sanders, Hatfield, PA (US); Graham F. Smith, Sudbury, MA (US)

(72) Inventors: Michael D. Altman, Needham, MA (US); Jason D. Brubaker, Cambridge, MA (US); Matthew L. Childers, Medfield, MA (US); Anthony Donofrio, Cambridge, MA (US); Thierry Fischmann, Scotch Plains, NJ (US); Craig R. Gibeau, Holliston, MA (US); Solomon D. Kattar, Wakefield, MA (US); Charles A. Lesburg, Newton, MA (US); Jongwon Lim, Lexington, MA (US); John K. F. Maclean, Ayrshire (GB); Umar F. Mansoor, Hopkinton, MA (US); Alan B. Northrup, Reading, MA (US); John M. Sanders, Hatfield, PA (US); Graham F. Smith, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/515,377

(22) PCT Filed: Sep. 25, 2015

(86) PCT No.: PCT/US2015/052116
§ 371 (c)(1),
(2) Date: Mar. 29, 2017

(87) PCT Pub. No.: WO2016/053772
PCT Pub. Date: Apr. 7, 2016

(65) Prior Publication Data
US 2017/0217981 A1 Aug. 3, 2017

Related U.S. Application Data

(60) Provisional application No. 62/057,653, filed on Sep. 30, 2014.

(51) Int. Cl.
C07D 491/08 (2006.01)
C07D 239/94 (2006.01)
A61K 31/517 (2006.01)
A61K 45/06 (2006.01)
C07D 239/88 (2006.01)
A61K 31/5377 (2006.01)
C07D 403/12 (2006.01)
C07D 401/12 (2006.01)
C07D 413/12 (2006.01)
A61K 31/538 (2006.01)
C07D 491/052 (2006.01)
A61K 31/5386 (2006.01)
C07D 491/048 (2006.01)
A61K 31/55 (2006.01)
C07D 405/12 (2006.01)

(52) U.S. Cl.
CPC .......... *C07D 491/08* (2013.01); *A61K 31/517* (2013.01); *A61K 31/538* (2013.01); *A61K 31/5377* (2013.01); *A61K 31/5386* (2013.01); *A61K 31/55* (2013.01); *A61K 45/06* (2013.01); *C07D 239/88* (2013.01); *C07D 239/94* (2013.01); *C07D 401/12* (2013.01); *C07D 403/12* (2013.01); *C07D 405/12* (2013.01); *C07D 413/12* (2013.01); *C07D 491/048* (2013.01); *C07D 491/052* (2013.01)

(58) Field of Classification Search
CPC .................................................... C07D 491/107
See application file for complete search history.

(56) References Cited

U.S. PATENT DOCUMENTS

| | | |
|---|---|---|
| 2005/0119273 A1 | 6/2005 | Lipford et al. |
| 2011/0021513 A1 | 1/2011 | Durand-Reville et al. |
| 2011/0166168 A1 | 7/2011 | Buchmann et al. |
| 2013/0274241 A1 | 10/2013 | Jorand-Lebrun et al. |

FOREIGN PATENT DOCUMENTS

| | | |
|---|---|---|
| WO | WO2014058685 | 4/2014 |
| WO | WO2016053769 | 4/2016 |
| WO | WO2016053772 | 4/2016 |
| WO | WO2016053770 | 7/2016 |
| WO | WO2016053771 | 4/2017 |

OTHER PUBLICATIONS

U.S. Appl. No. 15/515,396, filed Sep. 25, 2015.*
Pinedo et al. (2000).*
McMahon et al. (2000).*

* cited by examiner

*Primary Examiner* — Paul V Ward
(74) *Attorney, Agent, or Firm* — Gloria M. Fuentes; Matthew A. Leff

(57) ABSTRACT

The present invention relates to inhibitors of IRAK4 of Formula I and provides compositions comprising such inhibitors, as well as methods therewith for treating IRAK4-mediated or -associated conditions or diseases.

5 Claims, No Drawings

INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cyctokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4):221-237; and O'Neill, Biochem. Soc. Trans., 2000, 28(5):557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monymeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to inhibitors of IRAK4 of formula (I) and provides compositions comprising such inhibitors, as well as methods therewith for treating IRAK4-mediated or -associated conditions or diseases.

DETAILED DESCRIPTION OF THE INVENTION

The compounds of the instant invention are useful in the inhibition of the activity of IRAK4.

An embodiment of the instant invention is illustrated by the Formula I:

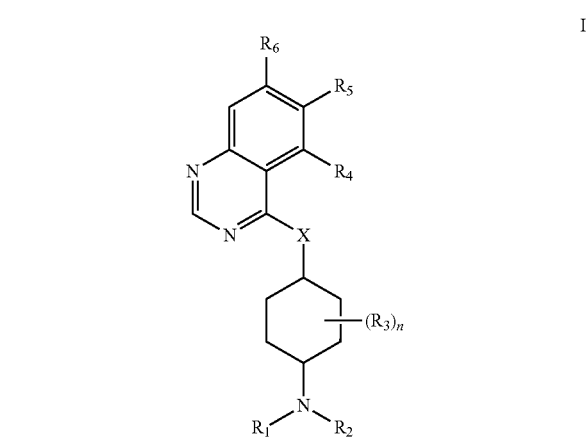

wherein:

X is NH or O;

b is 0 or 1;

n is 0, 1, 2, 3 or 4;

$R_1$ and $R_2$ are independently H and $(C_1-C_4)$alkyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;

$R_3$ is $(C_1-C_4)$alkyl wherein two adjacent alkyl groups can join together and form a bridged moiety of 3-6 carbon atoms;

$R_4$ is absent, halo or $O_b(C_1-C_4)$alkyl;

$R_5$ is halo, CN and $O(C_1-C_4)$alkyl, said alkyl optionally substituted with one or more substituents selected from CN and $(C=O)NH_2$;

$R_6$ is absent, halo, or $O(C_1-C_4)$alkyl;

$R_a$ is independently selected from halo, $CF_3$, $O_b(C_1-C_4)$alkyl, $SO_2(C_1-C_4)$alkyl, $C(O)$ $O_b(C_1-C_6)$alkyl, $(C=O)_b$heterocyclyl, wherein said alkyl can come together with another alkyl to form a bridged moiety and wherein said alkyl and heterocyclyl are optionally substituted with $R_b$; and $R_b$ is independently selected from OH, halo, $SO_2(C_1-C_4)$alkyl, $O_b(C_1-C_4)$alkyl, and heterocyclyl;

or a pharmaceutically acceptable salt or a stereoisomer thereof.

Another embodiment of the instant invention is illustrated by the Formula I:

wherein:

X is NH or O;

b is 0 or 1;

n is 0, 1, 2, 3 or 4;

$R_1$ and $R_2$ are independently H and $(C_1-C_4)$alkyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;

$R_3$ is methyl wherein two adjacent methyl groups can join together and form a bridged moiety of 3-6 carbon atoms;

$R_4$ is absent or $(C_1-C_4)$alkyl;

$R_5$ is halo, CN and $O(C_1-C_4)$alkyl, said alkyl optionally substituted with one or more substituents selected from CN and $(C=O)NH_2$;

$R_6$ is absent, halo, or $O(C_1-C_4)$alkyl;

$R_a$ is independently selected from halo, $CF_3$, $O_b(C_1-C_4)$alkyl, $SO_2(C_1-C_4)$alkyl, $C(O)$ $O_b(C_1-C_6)$alkyl, heterocyclyl, $C=O$-tetrahydrofuranyl, wherein said alkyl can come together with another alkyl for form a bridged moiety and wherein said alkyl and heterocyclyl are optionally substituted with $R_b$; and $R_b$ is independently selected from OH, halo, $SO_2(C_1-C_4)$alkyl, $O_b(C_1-C_4)$alkyl, morpholinyl and oxetanyl;

or a pharmaceutically acceptable salt or a stereoisomer thereof.

Another embodiment of the instant invention is illustrated by the Formula I:

wherein:

X is NH or O;

b is 0 or 1;

n is 0, 1 or 2;

$R_1$ and $R_2$ are independently H and $(C_1-C_4)$alkyl, or $R_1$ and $R_2$ can be taken together with the nitrogen to which they are attached to form morpholinyl, piperidinyl, azetidinyl, piperazinyl, pyrrolinyl, pyrhexahydrocyclopentaoxazinyl, hexahydropyranopyridinyl, hexahydrofuropyrrolyl, azabicyclooctyl, oxaazabicyclooctyl and azapanyl, said alkyl, morpholinyl, piperidinyl, azetidinyl, piperazinyl, pyrrolinyl, pyrhexahydrocyclopentaoxazinyl, hexahydropyranopyridinyl, hexahydrofuropyrrolyl, azabicyclooctyl, oxaazabicyclooctyl and azapanyl are optionally substituted with one or more substituents selected from $R_a$;

$R_3$ is methyl wherein two adjacent methyl groups can come together and form a bridged moiety;

$R_4$ is absent or methyl;

$R_5$ is selected from: Br, F, Cl, CN and $O(C_1-C_4)$alkyl, said alkyl optionally substituted with one or more substituents selected from CN and $(C=O)NH_2$;

$R_6$ is absent, halo, or $CH_3$;

$R_a$ is independently selected from F, $CF_3$, $O_b(C_1-C_4)$alkyl, $SO_2(C_1-C_4)$alkyl, $C(O)$ $O_b(C_1-C_6)$alkyl, heterocyclyl, $C=O$-tetrahydrofuran, wherein said alkyl can come together with another alkyl for form a bridged moiety and wherein said alkyl and heterocyclyl are optionally substituted with $R_b$; and $R_b$ is independently selected from OH, halo, $SO_2(C_1-C_4)$alkyl, $O_b(C_1-C_4)$alkyl, morpholinyl and oxetanyl;

or a pharmaceutically acceptable salt or a stereoisomer thereof.

A compound of the instant invention is selected from:

4-[(trans-4-aminocyclohexyl)amino]quinazoline-6-carbonitrile;

trans-N-(6-bromoquinazolin-4-yl)cyclohexane-1,4-diamine;

6-bromo-4-{[trans-4-(morpholin-4-yl)cyclohexyl]oxy}quinazoline;

6-bromo-N-[trans-4-(morpholin-4-yl)cyclohexyl]quinazolin-4-amine;

trans-N'-(6,7-dimethoxyquinazolin-4-yl)-N,N-dimethylcyclohexane-1,4-diamine;

trans-N'-(6,7-difluoroquinazolin-4-yl)-N,N-dimethylcyclohexane-1,4-diamine;

4-{[trans-4-(dimethylamino)cyclohexyl]amino}quinazoline-6-carbonitrile;

trans-N'-(6-bromoquinazolin-4-yl)-N,N-dimethylcyclohexane-1,4-diamine;

4-{[trans-4-(morpholin-4-yl)cyclohexyl]amino}quinazoline-6-carbonitrile;

6-methoxy-N-[trans-4-(morpholin-4-yl)cyclohexyl]quinazolin-4-amine;

6-fluoro-N-[trans-4-(morpholin-4-yl)cyclohexyl]quinazolin-4-amine;

N-[trans-4-(morpholin-4-yl)cyclohexyl]-6-(propan-2-yloxy)quinazolin-4-amine;

6-bromo-7-fluoro-N-[trans-4-(morpholin-4-yl)cyclohexyl]quinazolin-4-amine;

7-fluoro-6-methoxy-N-[trans-4-(morpholin-4-yl)cyclohexyl]quinazolin-4-amine;

6-chloro-N-[trans-4-(morpholin-4-yl)cyclohexyl]quinazolin-4-amine;

trans-N'-(6-methoxyquinazolin-4-yl)-N,N-dimethylcyclohexane-1,4-diamine;

[(4-{[trans-4-(dimethylamino)cyclohexyl]amino}quinazolin-6-yl)oxy]acetonitrile;

4-[(4-{[trans-4-(dimethylamino)cyclohexyl]amino}quinazolin-6-yl)oxy]butanenitrile;

2-[(4-{[trans-4-(dimethylamino)cyclohexyl]amino}quinazolin-6-yl)oxy]acetamide;

4-{[(1S,6R)-5-(morpholin-4-yl)bicyclo[4.1.0]hept-2-yl]amino}quinazoline-6-carbonitrile;

4-{[trans-4-(azetidin-1-yl)cyclohexyl]amino}quinazoline-6-carbonitrile;

4-({cis or trans-4-[(3R or S)-3-(trifluoromethyl)piperidin-1-yl]cyclohexyl}amino)quinazoline-6-carbonitrile;

4-({cis or trans-4-[(3R or S)-3-(trifluoromethyl)piperidin-1-yl]cyclohexyl}amino)quinazoline-6-carbonitrile;

4-({cis or trans-4-[(3R or S)-3-(trifluoromethyl)piperidin-1-yl]cyclohexyl}amino)quinazoline-6-carbonitrile;

4-({cis or trans-4-[(3R or S)-3-(trifluoromethyl)piperidin-1-yl]cyclohexyl}amino)quinazoline-6-carbonitrile;

4-{[cis-4-(azetidin-1-yl)cyclohexyl]amino}quinazoline-6-carbonitrile;

4-{[trans-4-(2,3-dimethylmorpholin-4-yl)cyclohexyl]
amino}quinazoline-6-carbonitrile;
4-{[cis-4-(2,3-dimethylmorpholin-4-yl)cyclohexyl]
amino}quinazoline-6-carbonitrile;
4-({trans-4-[(2R,6S)-2,6-dimethylmorpholin-4-yl]
cyclohexyl}amino)quinazoline-6-carbonitrile;
4-({trans-4[4-(methylsulfonyl)piperidin-1-yl]
cyclohexyl}amino)quinazoline-6-carbonitrile;
4-({trans-4-[(2R or 2S)-2-(hydroxymethyl)morpholin-4-yl]
cyclohexyl}amino)quinazoline-6-carbonitrile;
4-({trans-4-[(2R or 2S)-2-(hydroxymethyl)morpholin-4-yl]
cyclohexyl}amino)quinazoline-6-carbonitrile;
4-({trans-4-[3-(methylsulfonyl)pyrrolidin-1-yl]
cyclohexyl}amino)quinazoline-6-carbonitrile;
4-({trans-4-[(2S,6S or 2R,6R)-2,6-dimethylmorpholin-4-yl]
cyclohexyl}amino)quinazoline-6-carbonitrile;
4-({trans-4-[(2S,6S or 2R,6R)-2,6-dimethylmorpholin-4-yl]
cyclohexyl}amino)quinazoline-6-carbonitrile;
4-({trans-4-[(2S or 2R)-2-methylmorpholin-4-yl]
cyclohexyl}amino)quinazoline-6-carbonitrile;
4-({trans-4-[(2S or 2R)-2-methylmorpholin-4-yl]
cyclohexyl}amino)quinazoline-6-carbonitrile;
4-({trans-4-[(1S,4S)-2-oxa-5-azabicyclo[2.2.1]hept-5-yl]
cyclohexyl}amino)quinazoline-6-carbonitrile;
4-{[trans-4-(4-fluoropiperidin-1-yl)cyclohexyl]
amino}quinazoline-6-carbonitrile;
4-({trans-4-[4-(methylsulfonyl)piperazin-1-yl]
cyclohexyl}amino)quinazoline-6-carbonitrile;
4-({trans-4-[(2,2,2-trifluoroethyl)amino]cyclohexyl}amino)
quinazoline-6-carbonitrile;
4-({trans-4-[(2-methoxyethyl)amino]cyclohexyl}amino)
quinazoline-6-carbonitrile;
4-{[trans-4-(cyclopropylamino)cyclohexyl]
amino}quinazoline-6-carbonitrile;
4-({trans-4-[(4aS,7aS or 4aR,7aR)-hexahydrocyclopenta[b]
[1,4]oxazin-4(4aH)-yl]cyclohexyl}amino)quinazoline-6-
carbonitrile;
4-{[trans-4-(hexahydro-2H-pyrano[4,3-b]pyridin-1(5H)-yl)
cyclohexyl]amino}quinazoline-6-carbonitrile;
4-{[trans-4-(4-oxa-7-azaspiro[2.5]oct-7-yl)cyclohexyl]
amino}quinazoline-6-carbonitrile;
4-({trans-4-[2-(fluoromethyl)morpholin-4-yl]
cyclohexyl}amino)quinazoline-6-carbonitrile;
4-({trans-4-[(3S)-3-methylmorpholin-4-yl]
cyclohexyl}amino)quinazoline-6-carbonitrile;
4-{[trans-4-(3-methoxyazetidin-1-yl)cyclohexyl]
amino}quinazoline-6-carbonitrile;
4-{[trans-4-(4-methylpiperazin-1-yl)cyclohexyl]
amino}quinazoline-6-carbonitrile;
4-({trans-4-[(3R)-3-methylmorpholin-4-yl]
cyclohexyl}amino)quinazoline-6-carbonitrile;
4-({trans-4-[cyclopropyl(methyl)amino]cyclohexyl}amino)
quinazoline-6-carbonitrile;
4-{[trans-4-(3,3-difluoropiperidin-1-yl)cyclohexyl]
amino}quinazoline-6-carbonitrile;
4-({trans-4-[(3S)-3-hydroxypyrrolidin-1-yl]
cyclohexyl}amino)quinazoline-6-carbonitrile;
4-{[trans-4-(3-fluoropiperidin-1-yl)cyclohexyl]
amino}quinazoline-6-carbonitrile;
4-{[trans-4-(3-hydroxy-3-methylpyrrolidin-1-yl)cyclo-
hexyl]amino}quinazoline-6-carbonitrile;
4-({trans-4-[3-(morpholin-4-yl)azetidin-1-yl]
cyclohexyl}amino)quinazoline-6-carbonitrile;
4-({trans-4-[(3R)-3-hydroxypyrrolidin-1-yl]
cyclohexyl}amino)quinazoline-6-carbonitrile;
4-{[trans-4-(hexahydro-4H-furo[3,2-b]pyrrol-4-yl)cyclo-
hexyl]amino}quinazoline-6-carbonitrile;
4-({trans-4-[(3R)-3-methoxypyrrolidin-1-yl]
cyclohexyl}amino)quinazoline-6-carbonitrile;
4-({trans-4-[(3R or 3S)-3-(morpholin-4-ylmethyl)piperidin-
1-yl]cyclohexyl}amino)quinazoline-6-carbonitrile;
4-({trans-4-[(3R or 3S)-3-(morpholin-4-ylmethyl)piperidin-
1-yl]cyclohexyl}amino)quinazoline-6-carbonitrile;
4-({trans-4-[4-(morpholin-4-ylmethyl)piperidin-1-yl]
cyclohexyl}amino)quinazoline-6-carbonitrile;
4-{[trans-4-(pyrrolidin-1-yl)cyclohexyl]
amino}quinazoline-6-carbonitrile;
tert-butyl 4-{trans-4-[(6-cyanoquinazolin-4-yl)amino]
cyclohexyl}piperazine-1-carboxylate;
4-({trans-4-[3-(morpholin-4-ylmethyl)piperidin-1-yl]
cyclohexyl}amino)quinazoline-6-carbonitrile;
4-{[trans-4-(3-oxa-8-azabicyclo[3.2.1]oct-8-yl)cyclohexyl]
amino}quinazoline-6-carbonitrile;
4-({trans-4-[(2R or 2S)-2-(trifluoromethyl)morpholin-4-yl]
cyclohexyl}amino)quinazoline-6-carbonitrile;
4-({trans-4-[(2R or 2S)-2-(trifluoromethyl)morpholin-4-yl]
cyclohexyl}amino)quinazoline-6-carbonitrile;
4-({trans-4-[(1R,5S)-8-oxa-3-azabicyclo[3.2.1]oct-3-yl]
cyclohexyl}amino)quinazoline-6-carbonitrile;
4-{[trans-4-(2,2-dimethylmorpholin-4-yl)cyclohexyl]
amino}quinazoline-6-carbonitrile;
4-({trans-4-[(3R)-3-(propan-2-yl)morpholin-4-yl]
cyclohexyl}amino)quinazoline-6-carbonitrile;
4-{[trans-4-(4,4-difluoroazepan-1-yl)cyclohexyl]
amino}quinazoline-6-carbonitrile;
4-{[trans-4-(4,4-difluoropiperidin-1-yl)cyclohexyl]
amino}quinazoline-6-carbonitrile;
4-{[trans-4-(3-hydroxypyrrolidin-1-yl)cyclohexyl]
amino}quinazoline-6-carbonitrile;
4-[(4-{[trans-4-(dimethylamino)cyclohexyl]
amino}quinazolin-6-yl)oxy]butanamide;
7-fluoro-4-{[trans-4-(morpholin-4-yl)cyclohexyl]
amino}quinazoline-6-carbonitrile;
5-methyl-4-{[trans-4-(morpholin-4-yl)cyclohexyl]
amino}quinazoline-6-carbonitrile;
4-({trans-4-[4-(cyclopropylcarbonyl)piperazin-1-yl]
cyclohexyl}amino)quinazoline-6-carbonitrile;
4-{[trans-4-(4-acetylpiperazin-1-yl)cyclohexyl]
amino}quinazoline-6-carbonitrile;
4-({trans-4-[4-(2,2-dimethylpropanoyl)piperazin-1-yl]
cyclohexyl}amino)quinazoline-6-carbonitrile;
4-({trans-4-[4-(3-fluoro-2,2-dimethylpropanoyl)piperazin-
1-yl]cyclohexyl}amino)quinazoline-6-carbonitrile;
4-({trans-4-[4-(2-fluoro-2-methylpropanoyl)piperazin-1-yl]
cyclohexyl}amino)quinazoline-6-carbonitrile;
4-({trans-4-[4-(2,2-difluoropropanoyl)piperazin-1-yl]
cyclohexyl}amino)quinazoline-6-carbonitrile;
4-({trans-4-[4-(2-fluoropropanoyl)piperazin-1-yl]
cyclohexyl}amino)quinazoline-6-carbonitrile;
4-[(trans-4-{4-[(1-methylcyclopropyl)carbonyl]piperazin-
1-yl}cyclohexyl)amino]quinazoline-6-carbonitrile;
4-[(trans-4-{4-[(3-methyloxetan-3-yl)carbonyl]piperazin-1-
yl}cyclohexyl)amino]quinazoline-6-carbonitrile;
4-({trans-4-[4-(methoxyacetyl)piperazin-1-yl]
cyclohexyl}amino)quinazoline-6-carbonitrile;
4-[(trans-4-{4-[(2S)-tetrahydrofuran-2-ylcarbonyl]piper-
azin-1-yl}cyclohexyl)amino]quinazoline-6-carbonitrile;
4-({trans-4-[4-(difluoroacetyl)piperazin-1-yl]
cyclohexyl}amino)quinazoline-6-carbonitrile;
4-[(trans-4-{4-[(3-fluorocyclobutyl)carbonyl]piperazin-1-
yl}cyclohexyl)amino]quinazoline-6-carbonitrile;
4-[(trans-4-{4-[(2,2-difluorocyclopropyl)carbonyl]piper-
azin-1-yl}cyclohexyl)amino]quinazoline-6-carbonitrile;

4-({trans-4-[4-(cyclobutylcarbonyl)piperazin-1-yl] cyclohexyl}amino)quinazoline-6-carbonitrile;
4-({trans-4-[4-(cyclopentylcarbonyl)piperazin-1-yl] cyclohexyl}amino)quinazoline-6-carbonitrile;
4-({trans-4-[4-(cyclopropylacetyl)piperazin-1-yl] cyclohexyl}amino)quinazoline-6-carbonitrile;
4-({trans-4-[4-(oxetan-3-ylacetyl)piperazin-1-yl] cyclohexyl}amino)quinazoline-6-carbonitrile;
4-({trans-4-[4-(fluoroacetyl)piperazin-1-yl] cyclohexyl}amino)quinazoline-6-carbonitrile;
4-[(trans-4-{4-[cyclopropyl(hydroxy)acetyl]piperazin-1-yl}cyclohexyl)amino]quinazoline-6-carbonitrile;
4-[(trans-4-{4-[(3-hydroxycyclobutyl)carbonyl]piperazin-1-yl}cyclohexyl)amino]quinazoline-6-carbonitrile;
4-({trans-4-[4-(3-hydroxypropanoyl)piperazin-1-yl] cyclohexyl}amino)quinazoline-6-carbonitrile;
4-[(trans-4-{4-[(2R)-tetrahydrofuran-2-ylcarbonyl]piperazin-1-yl}cyclohexyl)amino]quinazoline-6-carbonitrile;
4-{[trans-1-methyl-4-(morpholin-4-yl)cyclohexyl] amino}quinazoline-6-carbonitrile;
4-{[trans-4-(4-fluoropiperidin-1-yl)-1-methylcyclohexyl] amino}quinazoline-6-carbonitrile;
4-{[trans-4-(3-hydroxypyrrolidin-1-yl)-1-methylcyclohexyl]amino}quinazoline-6-carbonitrile;
4-{[(1S,2S,5S,6R)-5-(4-fluoropiperidin-1-yl)bicyclo[4.1.0] hept-2-yl]amino}quinazoline-6-carbonitrile;
4-{[(1R,2R,4R or 1S,2S,4S)-2-methyl-4-(morpholin-4-yl) cyclohexyl]amino}quinazoline-6-carbonitrile;
4-{[(1S,2S,4S or 1R,2R,4R)-4-(4-fluoropiperidin-1-yl)-2-methylcyclohexyl]amino}quinazoline-6-carbonitrile; and
4-{[(1S,2R,4S or 1R,2S,4R)-2-methyl-4-(morpholin-4-yl) cyclohexyl]amino}quinazoline-6-carbonitrile;
or a pharmaceutically acceptable salt or stereoisomer thereof.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

This invention is also intended to encompass pro-drugs of the compounds disclosed herein. A prodrug of any of the compounds can be made using well known pharmacological techniques.

When any variable (e.g. $R_3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety. When $R_4$ and/or $R_6$ are "absent" it is understood that a hydrogen atom is present.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Scheme and Examples herein using appropriate isotopically-enriched reagents and/or intermediates.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. In some instances, two substituents are attached to the same carbon and come together to form a carbocyclic or heterocyclic ring (a spirocyclic ring system).

As used herein, "alkyl" is intended to include branched, cyclic and straight-chain saturated aliphatic hydrocarbon groups having the specified number of carbon atoms. For example, $C_1$-$C_4$, as in "($C_1$-$C_4$)alkyl" is defined to include groups having 1, 2, 3, and 4 carbon atoms in a linear, cyclic or branched arrangement. For example, "($C_1$-$C_4$)alkyl" specifically includes methyl, ethyl, n-propyl, i-propyl, n-butyl, t-butyl, i-butyl, cyclopropyl, and cyclobutyl. For example, $C_1$-$C_6$, as in "($C_1$-$C_6$)alkyl" is defined to include groups having 1, 2, 3, 4, 5 and 6 carbon atoms in a linear, cyclic or branched arrangement. For example, "($C_1$-$C_6$)alkyl" specifically includes methyl, ethyl, n-propyl, i-propyl, n-butyl, t-butyl, i-butyl, cyclopropyl cyclobutyl, cyclopenyl and cyclohexyl.

The term "heterocycle" as used herein is intended to mean a 3- to 10-membered aromatic or nonaromatic heterocycle containing from 1 to 4 heteroatoms selected from the group consisting of O, N and S, and includes monocyclic or bicyclic groups (fused, bridged or spirocyclic). "Heterocycle" therefore includes heteroaryls, as well as dihydro and tetrathydro analogs thereof. Further examples of "heterocycle" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

In one embodiment of Formula I, heterocycle is selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, optionally substituted with one to three substituents independently selected from $R_a$.

In another embodiment of Formula I, heterocycle is selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

In another embodiment of Formula I, heterocycle is selected from: oxazoline, oxetanyl, pyranyl, pyrazinyl, pyrazolyl, pyridazinyl, pyridyl, pyrimidyl, pyrrolyl, tetrazolyl, thiadiazolyl, thiazolyl, thienyl, triazolyl, azetidinyl, piperazinyl, piperidinyl, pyrrolidinyl, and morpholinyl.

In another embodiment of Formula I, heterocycle is selected from: azetidinyl, piperazinyl, piperidinyl, pyrrolidinyl, thiomorpholinyl, and morpholinyl.

As appreciated by those of skill in the art, "halo" or "halogen" as used herein is intended to include chloro (Cl), fluoro (F), bromo (Br) and iodo (I).

In another embodiment, X is NH.

In another embodiment, X is O.

In another embodiment, $R_3$ is methyl, wherein two adjacent methyl groups can join together and form a bridged moiety.

In another embodiment, n is 0, 1, or 2.

In another embodiment, n is 0 or 1.

In another embodiment, n is 1.

In another embodiment, n is 0.

Included in the instant invention is the free form of compounds of Formula I as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The preparation of the pharmaceutically acceptable salts described above and other typical pharmaceutically acceptable salts is more fully described by Berg et al., "Pharmaceutical Salts," J. Pharm. Sci., 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

According to another embodiment, the present invention provides a method of treating or reducing the severity of a disease in a patient by using a compound of Formulas I as described above, wherein said disease is selected from IRAK4 mediated pathologies, such as rheumatoid arthritis, multiple sclerosis, sepsis, osteoarthritis, inflammatory bowel disease, Parkinson's disease, cardiac contractile dysfunction, type I diabetes, type II diabetes or familial cold autoinflammatory syndrome, allergic disease, cancer, lupus, psoriasis, asthma or graft rejection.

The compounds of the invention find use in a variety of applications. As will be appreciated by those skilled in the art, the kinase activity of IRAK4 may be modulated in a variety of ways; that is, one can affect the phosphorylation/ activation of IRAK4 either by modulating the initial phosphorylation of the protein or by modulating the autophosphorylation of the other active sites of the protein. Alternatively, the kinase activity of IRAK4 may be modulated by affecting the binding of a substrate of IRAK4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of the invention may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer; hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

The compounds of the invention may be useful for the treatment of activated B-cell-like diffuse large B-cell lymphoma (ABC-DLBCL), chronic lymphocytic leukemia (CLL) and Waldenström's Macroglobulinemia.

The instant compounds are useful in combination with a known anti-cancer agent. Combinations of the presently disclosed compounds with anti-cancer agents are within the scope of the invention. Examples of such anti-cancer agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®);

daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Ferrara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of lupus.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of lupus.

The compounds of the instant invention are useful for the treatment of cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are:
2nd Gen. Precatalyst cataCXium® chloro[(di(1-adamantyl)-N-butylphosphine)-2-(2-aminobiphenyl)]palladium(II)
2nd Gen. Precatalyst X-Phos Chloro (2-dicyclohexylphosphino-2',4',6'-triisopropyl-1,1'-biphenyl)[2-(2'-amino-1, 1'-biphenyl)]palladium(II)
3rd Gen X-Phos Precatalys (2-Dicyclohexylphosphino-2',4', 6'-triisopropyl-1,1'-biphenyl)[2-(2'-amino-1,1'-biphenyl)] palladium(II) methanesulfonate
Ac Acetyl
ACN or MeCN acetonitrile
AcOH or HOAc acetic acid
APCI atmospheric-pressure chemical ionization aq aqueous
Bn benzyl
Boc or BOC tert-butoxycarbonyl
Brettphos 2-(dicyclohexylphosphino)3,6-dimethoxy-2',4',6'-triisopropyl-1,1'-biphenyl
Bu butyl
Bz benzoyl
calc'd calculated
cBu cyclobutyl
Cbz benyzloxycarbonyl
$CDCl_3$ chloroform-d
$CHCl_3$ Chloroform
cHep cycloheptyl
cHex cyclohexyl
cPen cyclopentyl
cPr cyclopropyl
DAST (diethylamino)sulfur trifluoride
dba dibenzylideneacetone
DBU 1,8-diazabicycloundec-7-ene
DCE 1,2-dichloroethane
DCM dichloromethane
DIBAL or Dibal-H diisobutylaluminum hydride
DIEA or Hünig's base N,N-diisopropylethylamine
DMA 1,2-dimethylacetamide
DMAP 4-dimethylaminopyridine
DMEA Dimethylethylamine
DMSO Dimethylsulfoxide
DMF dimethylformamide
DMP Dess-Martin periodinane (1,1,1-triacetoxy)-1,1-dihydro-1,2-benziodoxol-3(1H)-one
DMSO dimethyl sulfoxide
dppf 1,1'-bis(diphenylphosphino)ferrocene
DTT dithiothreitol
EDC 1-ethyl-3-(3-dimethylaminopropy)carbodiimide
EDTA ethylenediamine tetraacetic acid
ESI electrospray ionization
Et ethyl
EtOH ethanol
EtOAc ethyl acetate
g grams
GST glutathione S-transferase
h hour
HATU N,N,N',N'-tetramethyl-O-(7-azabenzotriazol-1-yl)uronium hexafluorophosphate
HCl hydrochloric acid
HMDS 1,1,1,3,3,3-hexamethyldisilazane
HOBt 1-hydroxybenzotriazole
HPLC high-performance liquid chromatography
IPA or iPrOH isopropanol
iPr isopropyl
LC liquid chromatography
LCMS liquid chromatography mass spectrometry
LDA lithium diisopropylamide
M molar
mCPBA m-choroperoxybenzoic acid
Me methyl
MeOH methanol
mg milligrams
min minute
μL microliters
mL milliliters
mmol millimoles
MS mass spectrometry
Ms methanesulfonyl (mesyl)
MTBE methyl tert-butyl ether
NBS N-bromosuccinimide
NMR nuclear magnetic resonance spectroscopy
OAc Acetate
obsv'd observed
$Pd(PPh_3)_4$ palladium(0) tetrakis-triphenylphosphine
$Pd(dppf)Cl_2$ 1,1'-bis(diphenylphosphino)ferrocene]dichloro palladium(II)
Ph phenyl
$(PinB)_2$ 4,4,4',4',5,5,5',5'-octamethyl-2,2'-bi(1,3,2-dioxaborolane)
$POCl_3$ phosphorous oxychloride
Pr propyl
PS polystyrene
rac racemic mixture
RT or rt room temperature (ambient, about 25° C.)
sat saturated
SFC supercritical fluid chromatography
Si-DPP-Pd SiliaCat®DPP-Pd
S-phos 2-dicyclohexylphosphino-2',6'-dimethoxybiphenyl
T3P Propylphosphonic anhydride
TBAF tert-butyl ammonium fluoride
TBDPS tert-butyl diphenyl silyl
TBS or TBDMS tert-butyldimethyl silyl
TBSCl tert-butyldimethylsilyl chloride
tBu tert-butyl
tBu X-phos 2-di-tert-butylphosphino-2',4',6'-triisopropylbiphenyl
TEA triethylamine ($Et_3N$)
TFA trifluoroacetic acid
TFAA trifluoroacetic anhydride
THF tetrahydrofuran
TLC thin layer chromatography
TMS trimethylsilyl
Tris tris(hydroxymethyl)aminomethane
Ts toluenesulfonyl (tolyl)
TSA p-toluenesulfonic acid
X-phos 2-dicyclohexylphosphino-2',4',6'-triisopropylbiphenyl
Xantphos 4,5-bis(diphenylphosphino)-9,9-dimethylxanthene General Synopsis of Reaction Schemes The following General Reaction Schemes, Schemes 1 to 8, provide useful details for preparing the instant compounds. The requisite intermediates are in some cases commercially available or can be prepared according to literature procedures. The illustrative General Reaction Schemes below are not limited by the compounds listed or by any particular substituents employed for illustrative purposes. Substituent labeling (i.e. R groups) as shown in the Reaction Schemes do not necessarily correlate to that used in the claims and often, for clarity, a single substituent is shown attached to the compound where multiple substituents are allowed under the definitions of Formula I hereinabove.

Scheme 1
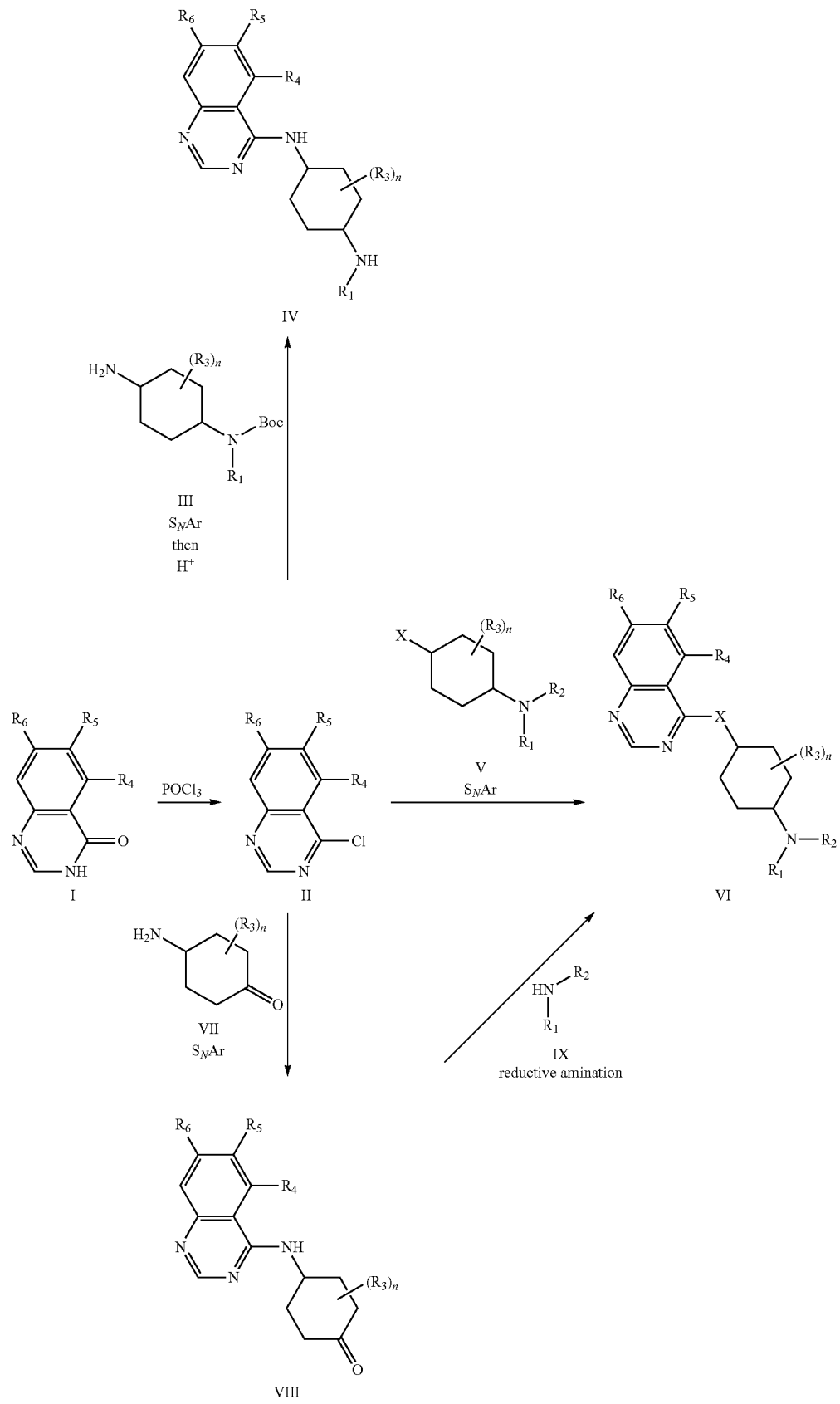

Compounds of formula IV are prepared by the reaction of 4-chloroquinazolines (II) with substituted diamines (III) via $S_NAr$ conditions followed by acidic deprotection of the Boc protecting group. Additionally, compounds of formula VI are prepared by the reaction of 4-chloroquinazolines (II) with the desired amines or alcohols (V) via $S_NAr$ conditions.

Compounds of formula VI are also obtained by the reductive amination of cyclohexanones (VIII) with substituted amines (IX). Cyclohexanones (VIII) are prepared by the reaction of 4-chloroquinazolines (II) with the desired substituted 4-aminocyclohexanones (VII) via $S_NAr$ conditions. Substituted 4-chloroquinazolines (II) are prepared from substituted 4-quinazolinones (I) by chlorination with $POCl_3$.

Scheme 2

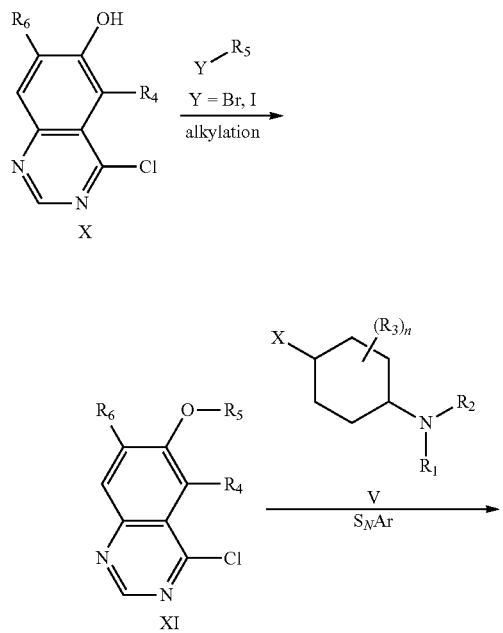

Scheme 3

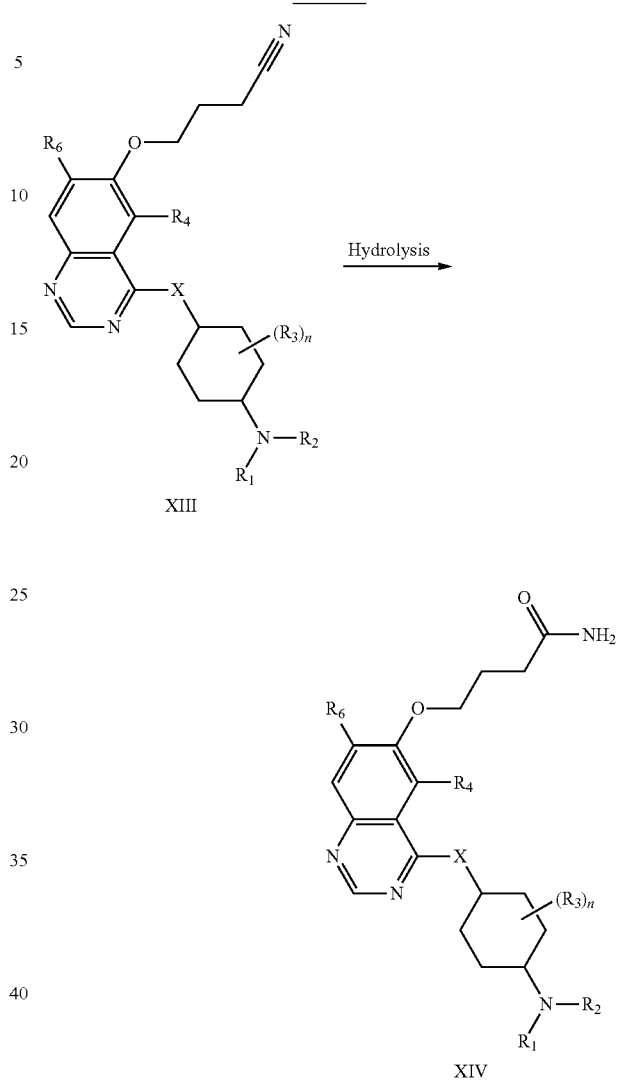

Compounds of formula XIV are prepared from substitued quinazolines (XIII) by hydrolysis of the nitrile. Substituted quinazolines (XIII) are prepared according to Scheme 2.

Scheme 4

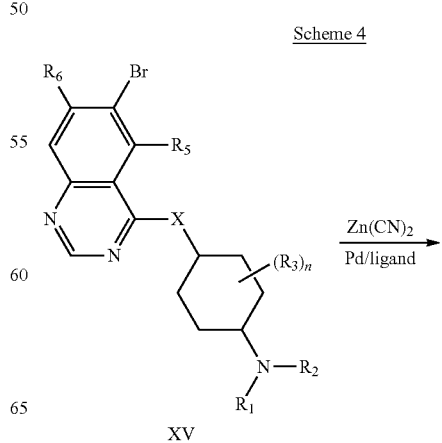

Compounds of formula XII are prepared by the reaction of 4-chloroquinazolines (XI) with desired amines or alcohols (V) via $S_NAr$ conditions. Substituted 4-chloroquinazolines (XI) are prepared from substituted 4-chloroquinazolin-6-ols (X) via alkylating conditions.

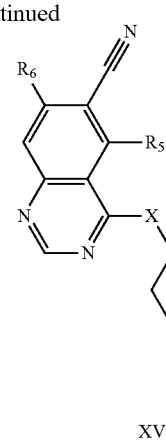

XVI

Compounds of formula XVI are prepared from substitued quinazolines (XV) by palladium-mediated cyanation. Substituted quinazolines (XV) are prepared according to Scheme 1.

Scheme 5

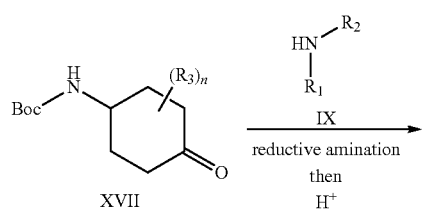

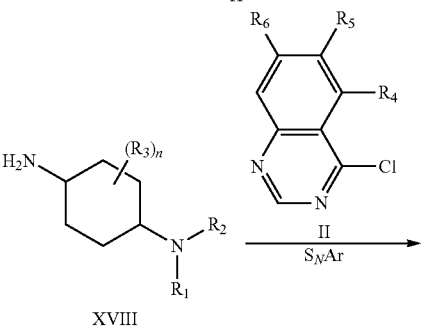

XIV

Compounds of formula XIV are prepared by the reaction of 4-chloroquinazolines (II) with substituted cyclohexylamines (XVIII) via S$_N$Ar conditions. Substituted cyclohexylamines (XVIII) are prepared by the reductive amination of protected 4-aminocyclohexanones (XVII) with substituted amines (IX) followed by acidic deprotection of the Boc protecting group.

Scheme 6

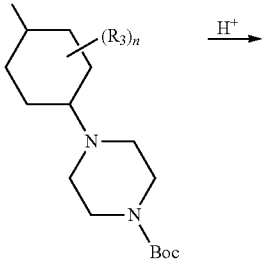

XX

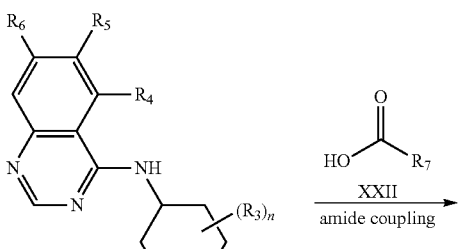

XXI

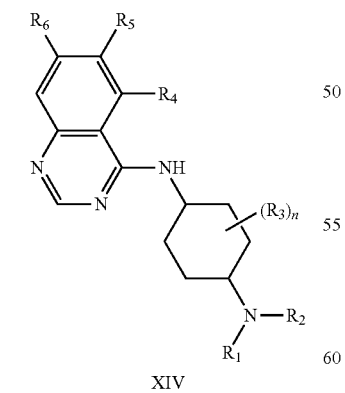

XXIII

Compounds of formula XIX are prepared from piperazines (XXI) by amidation conditions. Piperazines (XXI) are prepared by acidic deprotection of 4-aminoquinazolines (XX). 4-Aminoquinazolines are prepared according to the reductive amination route in Scheme 1.

Scheme 7
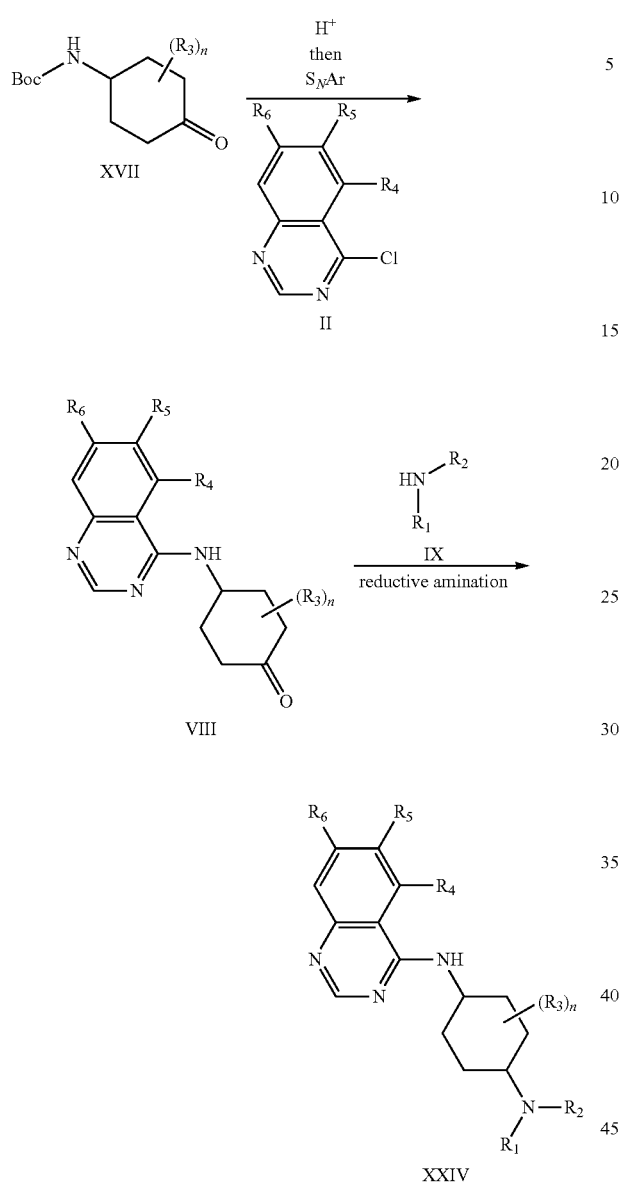
Compounds of formula XXIV are prepared by the reductive amination of cyclohexanones (VIII) with substituted amines (IX). Cyclohexanones (VIII) are obtained by acitic deprotection of protected 4-aminocyclohexanones (XVII) followed by reaction with 4-chloroquinazolines (II) via $S_NAr$ conditions.
Scheme 8
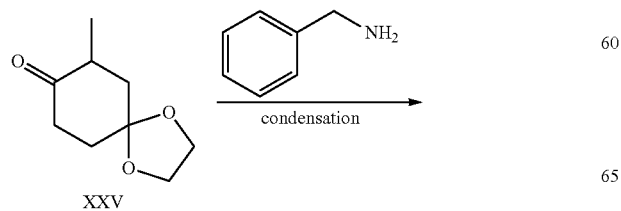
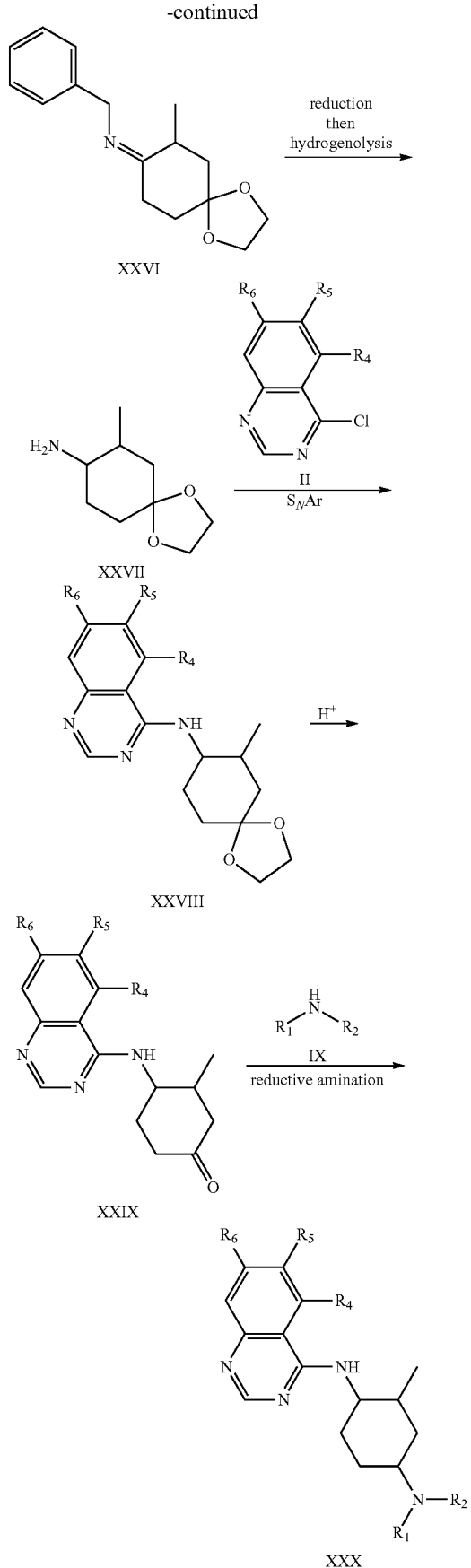

Compounds of formula XXX are prepared by the reductive amination of cyclohexanones (XXIX) with substituted amines (IX). Cyclohexanones (XXIX) are obtained from acetic deprotection of cyclic ketals (XXVIII). Cyclic ketals are prepared by the reaction of 4-chloroquinazolines (II) with cyclohexylamine (XXVII) via $S_NAr$ conditions. Cyclohexylamine (XXVII) is prepared by reduction of imine (XXVI) followed by hydrogenolysis of the benzyl group Imine (XXVI) is obtained from condensation of cyclohexanone (XXV) with benzylamine.

Intermediate 1-1

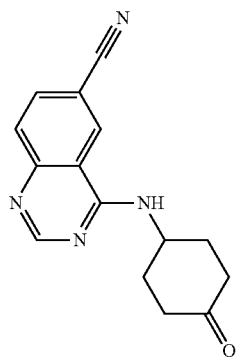 [SMILES: N#Cc1ccc2ncnc(NC3CCC(=O)CC3)c2c1]

4-((4-oxocyclohexyl)amino)quinazoline-6-carbonitrile (Scheme 1)

4-Chloroquinazoline-6-carbonitrile (1.10 g, 5.78 mmol), 4-aminocyclohexanone hydrochloride (1.30 g, 8.66 mmol), DIEA (8.07 mL, 46.2 mmol), and DMA (60 mL) were added to a round bottom flask. The contents of the flask were allowed to stir for 4 h at rt. The reaction mixture was concentrated under reduced pressure. MeOH was added resulting in formation of a precipitate, which was collected by vacuum filtration and dried under reduced pressure to afford the title compound. MS: 267 (M+1). $^1$H NMR (600 MHz, dmso) δ 8.94 (s, 1H), 8.59 (s, 1H), 8.39 (s, 1H), 8.06 (d, J=8.6, 1H), 7.76 (d, J=8.6, 1H), 4.71-4.61 (m, 1H), 2.58-2.50 (m, 2H), 2.30 (d, J=14.7, 2H), 2.22-2.15 (m, 2H), 1.89-1.79 (m, 2H).

Intermediate 2-1

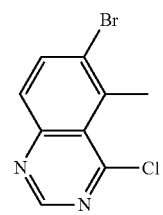

6-bromo-4-chloro-5-methylquinazoline (Scheme 1)

Phosphorus oxychloride (5.07 ml, 54.4 mmol) and N,N-diisopropylethylamie (0.095 mL, 0.540 mmol) were added to a microwave vial containing 6-bromo-5-methylquinazolin-4-ol (0.13 g, 0.54 mmol). The vial was sealed and then heated at 80° C. for 18 h. Upon completion of the reaction, the solvent was removed under reduced pressure. The residue was further dried by addition of toluene, followed by further solvent removal under reduced pressure. The title compound was obtained without further purification. MS: 256/258 (M+1).

Intermediate 3-1

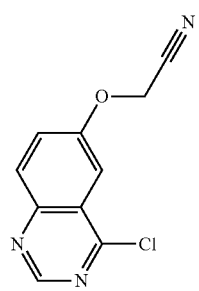 [SMILES: N#CCOc1ccc2ncnc(Cl)c2c1]

[(4-chloroquinazolin-6-yl)oxy]acetonitrile (Scheme 2)

Bromoacetonitrile (0.075 ml, 1.107 mmol) was added to a solution of 4-chloroquinazolin-6-ol (0.1 g, 0.554 mmol) and cesium carbonate (0.361 g, 1.107 mmol) in DMF (2.77 mL), all under an atmosphere of argon. The reaction was stirred for 3 h at rt. The reaction was diluted with water and extracted with EtOAc (3×), the combined organic layers were then washed with water and brine, dried over anhydrous sodium sulfate, filtered and the material was used without further purification. MS: 220 (M+1).

The following intermediates in Table 1 were prepared in an analogous manner to that described for Intermediate 3-1and in general scheme 2.

TABLE 1

| Intermediate Number | Structure | Chemical Name | MS (M + 1) |
| --- | --- | --- | --- |
| 3-2 | 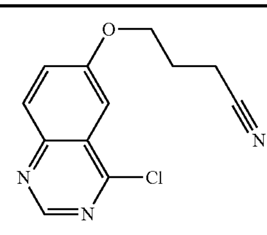 | 4[(4-chloroquinazolin-6-yl)oxy]butanenitrile | Calc'd 248.0, found 248 |

TABLE 1-continued

| Intermediate Number | Structure | Chemical Name | MS (M + 1) |
|---|---|---|---|
| 3-3 | 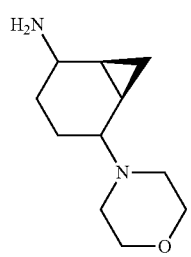 [SMILES: NC1CCC(N2CCOCC2)[C@@H]2C[C@H]12] | 2-[(4-chloroquinazoin-6-yl)oxy]acetamide | Calc'd 238.0, found 238 |

Intermediate 4-1

(1S,6R)-5-(morpholin-4-yl)bicyclo[4.1.0]heptan-2-amine (Scheme 5)

A 20 mL scintillation vial was charged with morpholine (0.043 mL, 0.488 mmol) and 1,2-dichloroethane (4.5 mL). tert-Butyl ((1S,2S,6R)-5-oxobicyclo[4.1.0]heptan-2-yl)carbamate (100 mg, 0.444 mmol) and acetic acid (0.127 mL, 2.22 mmol) were added and the reaction mixture was stirred at rt for 5 min. Sodium triacetoxyborohydride (329 mg, 1.55 mmol) was added and the reaction mixture was stirred at rt for an additional 16 h. Desired product formation was confirmed by LCMS analysis. The mixture was diluted with dichloromethane (5 mL), washed with aqueous sodium hydrogen carbonate (saturated, 2×5 mL), dried (MgSO$_4$), filtered and the solvent evaporated under reduced pressure. The resulting residue was taken up in a mixture of dioxane (1 mL) and water (0.2 mL). A solution of 4 N hydrochloric acid (2 mL, 8 mmol) in dioxane was added and the resulting mixture stirred at rt for 1 h. Full hydrolysis was confirmed by LCMS analysis. The reaction mixture was concentrated, taken up in water/acetonitrile (1:1, 5 mL) and lyophillized overnight to afford (1S,6R)-5-(morpholin-4-yl)bicyclo[4.1.0]heptan-2-amine. MS: 197 (M+1).

Intermediate 5-1

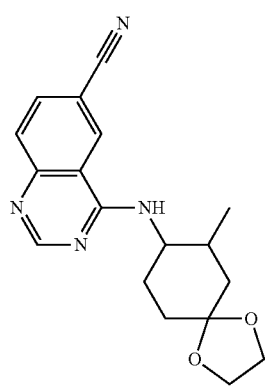 [SMILES: CC1CC2(CCC1Nc1ncnc3ccc(C#N)cc13)OCCO2]

4-{[(7S,8S or 7R,8R)-7-methyl-1,4-dioxaspiro[4.5]dec-8-yl]amino}quinazoline-6-carbonitrile and 4-{[(7S,8R or 7R,8S)-7-methyl-1,4-dioxaspiro[4.5]dec-8-yl]amino}quinazoline-6-carbonitrile (Scheme 8)

Step 1: N-(7-Methyl-1,4-dioxaspiro[4.5]decan-8-ylidene)-1-phenylmethanamine

A solution of titanium tetrachloride in DCM (1M, 5.88 mL, 5.88 mmol) was added dropwise to a stirred ice-cooled solution of triethylamine (9.83 mL, 70.5 mmol) and benzylamine (1.54 mL, 14.1 mmol) in DCM (10 mL) under an inert atmosphere. The reaction was warmed to ambient temperature and then refluxed. A solution of 7-methyl-1,4-dioxaspiro[4.5]decan-8-one (2.00 g, 11.8 mmol) in DCM (10 mL) was added and the reaction mixture was refluxed for an additional 16 hours. The reaction was cooled to room temperature and then diluted with diethyl ether (20 mL). The formed precipitate was filtered off and washed through with diethyl ether. The filtrate was concentrated and the resulting brown oil taken forward to the next step. MS: 260 (M+1).

Step 2: N-Benzyl-7-methyl-1,4-dioxaspiro[4.5]decan-8-amine

To a solution of N-(7-methyl-1,4-dioxaspiro[4.5]decan-8-ylidene)-1-phenylmethanamine (3.11 g, 12.0 mmol) in ethanol (30 mL) cooled to −78° C., was added sodium borohydride (0.227 g, 6.00 mmol). The reaction mixture was stirred for 30 minutes and then warmed to −20° C. Saturated sodium potassium tartrate (5 mL) was added and the ethanolic solution concentrated. The resulting residue was diluted with water, basified with sodium bicarbonate solution and extracted with ethyl acetate (2×10 mL). The organic layer was washed with brine (2×10 mL), dried (MgSO$_4$), filtered and the solvent was evaporated under reduced pressure. The resulting residue was purified by column chromatography on silica gel ISCO; 80 g prepacked, (0-60% hexanes/ethyl acetate) to afford a mixture of the cis- and trans-diastereomers. MS: 262 (M+1).

Step 3: 7-Methyl-1,4-dioxaspiro[4.5]decan-8-amine

To a 100 mL round bottom flask charged with N-benzyl-7-methyl-1,4-dioxaspiro[4.5]decan-8-amine (0.678 g, 2.59 mmol) and methanol (20 mL) was added palladium hydroxide on carbon (0.091 g, 0.130 mmol). The flask was evacuated and back-filled with hydrogen gas using a balloon. This procedure was carried out another two times and the reaction mixture was stirred under a hydrogen atmosphere for 16 hours. The palladium was filtered by passing through a plug of celite and washing through with methanol. The filtrate was concentrated to afford the title compound. MS: 172 (M+1).

Step 4: 4-{[(7S,8S or 7R,8R)-7-methyl-1,4-dioxaspiro[4.5]dec-8-yl]amino}quinazoline-6-carbonitrile and 4-{[(7S,8R or 7R,8S)-7-methyl-1,4-dioxaspiro[4.5]dec-8-yl]amino}quinazoline-6-carbonitrile A 20 mL scintillation vial was charged with 4-chloroquinazoline-6-carbonitrile (0.275 g, 1.45 mmol), 7-methyl-1,4-dioxaspiro[4.5]decan-8-amine (0.422 g, 2.03 mmol) and DMA (15 mL). DIEA (2.03 mL, 11.6 mmol) was added, the vial was capped and the contents stirred at room temperature for 16 hours. The volatiles were removed in vacuo, the resulting residue diluted with dichloromethane/iPrOH (10:1, 10 mL), washed with aqueous ammonium chloride (saturated, 2×10 mL), dried (MgSO$_4$), filtered and the solvent was evaporated under reduced pressure. The resulting residue was purified by column chromatography on silica gel ISCO; 24 g prepacked, (0-66% hexanes/ethyl acetate) to afford 4-{[(7S,8S or 7R,8R)-7-methyl-1,4-dioxaspiro[4.5]dec-8-yl]amino}quinazoline-6-carbonitrile, MS: 325 (M+1) $^1$H NMR (600 MHz, CDCl$_3$): δ 8.69 (s, 1H); 8.18 (s, 1H); 7.92-7.87 (m, 2H); 6.00 (br s, 1H); 4.67-4.62 (m, 1H); 4.04-3.94 (m, 4H); 2.33-2.29 (m, 1H); 2.06-2.03 (m, 1H); 1.93-1.86 (m, 1H); 1.81 (dd, J=13.9, 4.3 Hz, 1H); 1.72 (dd, J=10.0, 4.7 Hz, 2H); 1.64 (t, J=12.7 Hz, 1H); 1.01 (d, J=7.0 Hz, 3H) and 4-{[(7S,8R or 7R,8S)-7-methyl-1,4-dioxaspiro[4.5]dec-8-yl]amino}quinazoline-6-carbonitrile. MS: 325 (M+1) $^1$H NMR (600 MHz, CDCl$_3$): δ 8.67 (s, 1H); 8.27 (br s, 1H); 7.92 (s, 1H); 7.87 (d, J=8.5 Hz, 1H); 4.18-4.13 (m, 1H); 3.99-3.93 (m, 4H); 2.13-2.09 (m, 1H); 1.96 (br s, 1H); 1.87 (dt, J=13.5, 3.5 Hz, 1H); 1.85-1.80 (m, 1H); 1.75 (td, J=13.5, 4.1 Hz, 1H); 1.64 (q, J=12.8 Hz, 1H); 1.53 (t, J=13.0 Hz, 1H): 0.99 (d, J=6.6 Hz, 3H).

Example 1-1

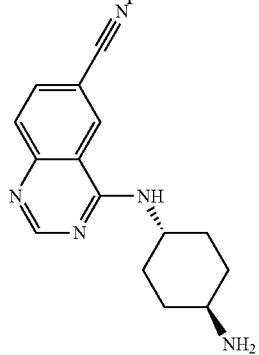

4-[(Trans-4-aminocyclohexyl)amino]quinazoline-6-carbonitrile (Scheme 1)

Step 1: tert-butyl {trans-4-[(6-cyanoquinazolin-4-yl)amino]cyclohexyl}carbamate 4-Chloroquinazoline-6-carbonitrile (50 mg, 0.264 mmol), Cs$_2$CO$_3$ (301 mg, 0.923 mmol), and tert-butyl ((trans)-4-aminocyclohexyl)carbamate bis-hydrochloride (91.0 mg, 0.316 mmol) were added to a vial, and then DMF (2 mL) was added. The vial was sealed and stirred overnight at rt. Water was added resulting in formation of a precipitate, which was collected via vacuum filtration, and washed with diethyl ether. The collected solids were dried under reduced pressure to afford the title compound. MS: 368 (M+1).

Step 2: 4-[(trans-4-aminocyclohexyl)amino]quinazoline-6-carbonitrile

Tert-butyl ((trans)-4-((6-cyanoquinazolin-4-yl)amino)cyclohexyl)carbamate (22 mg, 0.060 mmol) was weighed directly into a vial. The contents of the vial were dissolved in dichloromethane (1 mL), and then 4N HCl in dioxane (200 μl, 0.800 mmol) was added. The vial was sealed and its contents were stirred for 2 h at rt. The reaction mixture was concentrated under reduced pressure. The residue was dissolved in DMSO (1 mL), filtered, and purified by mass triggered reverse phase HPLC (ACN/water with 0.1% NH$_4$OH modifier) to afford the title compound. MS: 268 (M+1). 1H NMR (600 MHz, dmso) δ 8.90 (s, 1H), 8.51 (s, 1H), 8.21 (d, J=7.4, 1H), 8.01 (d, J=8.5, 1H), 7.72 (d, J=8.6, 1H), 4.15-4.01 (m, 1H), 2.63-2.54 (m, 1H), 1.96-1.86 (m, 2H), 1.86-1.75 (m, 2H), 1.44-1.34 (m, 2H), 1.21-1.09 (m, 2H).

The following example in Table 2 was prepared in an analogous manner to that described in Example 1 and in general scheme 1.

TABLE 2

| Example # | Structure | Chemical Name | MS (M + 1) |
|---|---|---|---|
| 1-2 | ![structure] | trans-N-(6-bromoquinazolin-4-yl)cyclohexane-1,4-diamine | Calc'd 321.0, found 321/323 |

Example 2-1

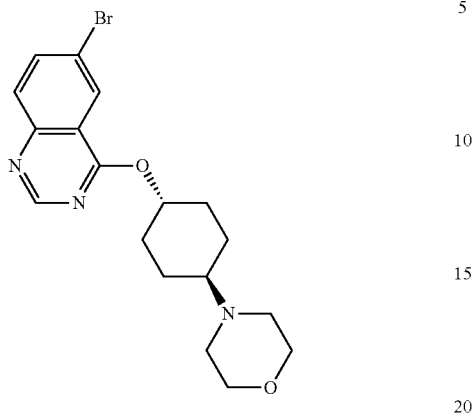

6-Bromo-4-{[trans-4-(morpholin-4-yl)cyclohexyl]oxy}quinazoline (Scheme 1)

Trans-4-morpholinocyclohexanol (0.134 g, 0.723 mmol) was dissolved in THF (10.95 ml) and added to a slurry of 6-bromo-4-chloroquinazoline (0.16 g, 0.657 mmol) in N,N-dimethylformamide (0.349 mL). The reaction was cooled to 0° C. and sodium hydride (0.053 g, 1.31 mmol) was added to the reaction mixture at 0° C. and the reaction was allowed to stir at rt for 18 h. The reaction was quenched with saturated aqeuous sodium bicarbonate and the aqueous layer was extracted with 25% IPA/CHCl$_3$ (2×), dried over anhydrous sodium sulfate, filtered and purified by mass triggered reverse phase HPLC (ACN/water with 0.1% NH$_4$OH modifier) to afford the title compound. MS: 392/394 (M+1). $^1$H NMR (600 MHz, dmso) δ 8.78 (s, 1H), 8.21 (d, J=2.2, 1H), 8.04 (dd, J=2.3, 8.9, 1H), 7.82 (d, J=8.9, 1H), 5.26-5.17 (m, 1H), 3.57-3.51 (m, 4H), 2.46-2.42 (m, 4H), 2.30-2.22 (m, 1H), 2.21-2.13 (m, 2H), 1.92-1.83 (m, 2H), 1.62-1.50 (m, 2H), 1.46-1.33 (m, 2H).

Example 2-2

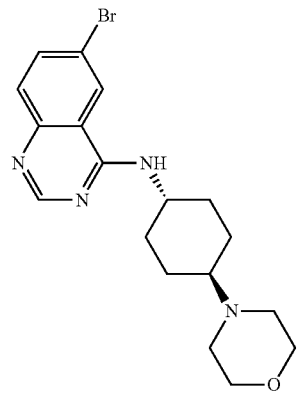 [SMILES: Brc1ccc2ncnc(N[C@H]3CC[C@H](N4CCOCC4)CC3)c2c1]

6-Bromo-N-[trans-4-(morpholin-4-yl)cyclohexyl]quinazolin-4-amine (Scheme 1)

To a solution of (trans)-4-morpholinocyclohexanamine bishydrochloride (50.00 g, 226.51 mmol) and 6-bromo-4-chloroquinazoline (66.18 g, 271.81 mmol) in DMF (600 mL) was added a solution of TEA (137.52 g, 1.36 mol) drop-wise at rt under N$_2$. The reaction mixture was heated to 90° C. for 16 h, and then cooled to rt, poured into ice/water and filtered. The filtered cake washed with water and dried to give the title compound as a solid. MS: 391/393 (M+1). $^1$H NMR (600 MHz, cd3od) δ 8.43 (d, J=2.1, 1H), 8.41 (s, 1H), 7.85 (dd, J=2.1, 8.9, 1H), 7.57 (d, J=8.9, 1H), 4.22-4.12 (m, 1H), 3.74-3.65 (m, 4H), 2.66-2.55 (m, 4H), 2.36-2.25 (m, 1H), 2.19-2.09 (m, 2H), 2.09-2.00 (m, 2H), 1.54-1.38 (m, 4H).

The following examples in Table 3 were prepared in an analogous manner of those described in Example 2-1 and Example 2-2 and in general schemes 1, 2 and 5 using intermediates of general structure II and XI which were either commercial or prepared as described herein.

TABLE 3

| Example # | Structure | Chemical Name | MS (M + 1) |
|---|---|---|---|
| 2-3 | (structure shown) | trans-N'-(6,7-dimethoxyquinazolin-4-yl)-N,N-dimethylcyclohexane-1,4-diamine | Calc'd 331.0, found 331 |

TABLE 3-continued

| Example # | Structure | Chemical Name | MS (M + 1) |
|---|---|---|---|
| 2-4 | 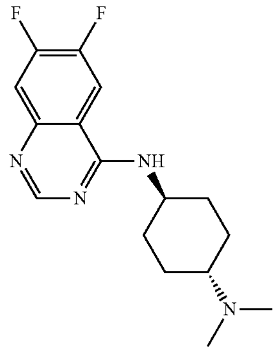 [SMILES: CN(C)[C@H]1CC[C@H](Nc2ncnc3cc(F)c(F)cc23)CC1] | trans-N'-(6,7-difluoroquinazolin-4-yl)-N,N-dimethylcyclohexane-1,4-diamine | Calc'd 307.0, found 307 |
| 2-5 | 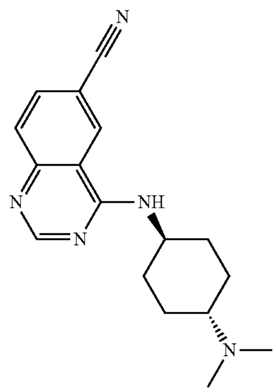 [SMILES: CN(C)[C@H]1CC[C@H](Nc2ncnc3ccc(C#N)cc23)CC1] | 4-{[trans-4-(dimethylamino)cyclohexyl]amino}quinazoline-6-carbonitrile | Calc'd 296.0, found 296 |
| 2-6 | 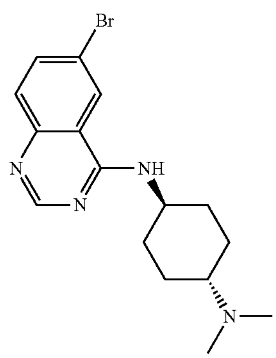 [SMILES: CN(C)[C@H]1CC[C@H](Nc2ncnc3ccc(Br)cc23)CC1] | trans-N'-(6-bromoquinazolin-4-yl)-N,N-dimethylcyclohexane-1,4-diamine | Calc'd 349.0, found 349/351 |
| 2-7 | 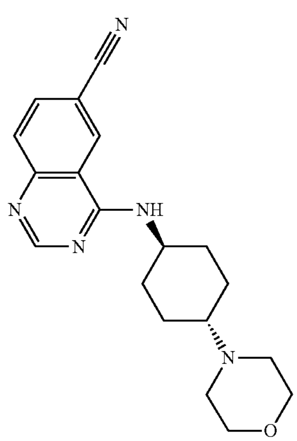 [SMILES: N#Cc1ccc2ncnc(N[C@H]3CC[C@H](N4CCOCC4)CC3)c2c1] | 4-{[trans-4-(morpholin-4-yl)cyclohexyl]amino}quinazoline-6-carbonitrile | Calc'd 338.0, found 338 |

TABLE 3-continued

| Example # | Structure | Chemical Name | MS (M + 1) |
|---|---|---|---|
| 2-8 | 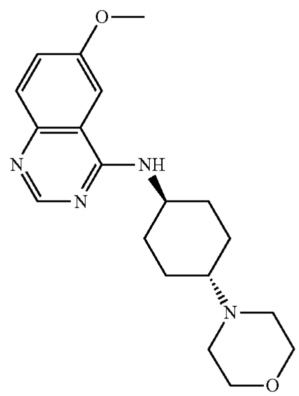 | 6-methoxy-N-[trans-4-(morpholin-4-yl)cyclohexyl]quinazolin-4-amine | Calc'd 343.0, found 343 |
| 2-9 | 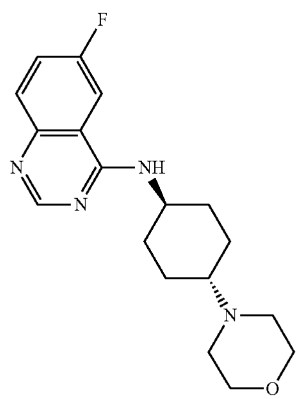 [SMILES: Fc1ccc2ncnc(N[C@H]3CC[C@H](N4CCOCC4)CC3)c2c1] | 6-fluoro-N-[trans-4-(morpholin-4-yl)cyclohexyl]quinazolin-4-amine | Calc'd 331.0, found 331 |
| 2-10 | 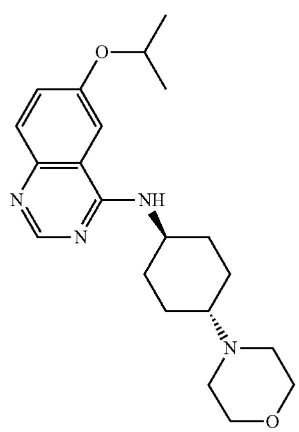 [SMILES: CC(C)Oc1ccc2ncnc(N[C@H]3CC[C@H](N4CCOCC4)CC3)c2c1] | N-[trans-4-(morpholin-4-yl)cyclohexyl]-6-(propan-2-yloxy)quinazolin-4-amine | Calc'd 371.0, found 371 |
| 2-11 | 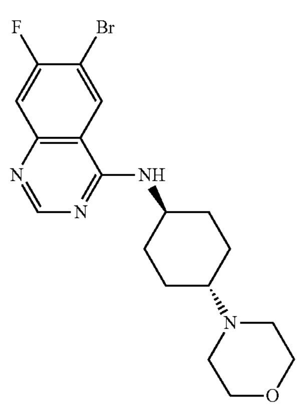 [SMILES: Fc1cc2ncnc(N[C@H]3CC[C@H](N4CCOCC4)CC3)c2cc1Br] | 6-bromo-7-fluoro-N-[trans-4-(morpholin-4-yl)cyclohexyl]quinazolin-4-amine | Calc'd 409.0, found 409/411 |

TABLE 3-continued

| Example # | Structure | Chemical Name | MS (M + 1) |
|---|---|---|---|
| 2-12 | 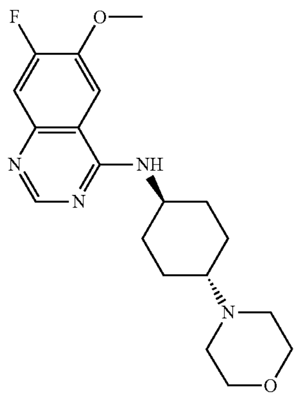 [SMILES: COc1cc2c(N[C@H]3CC[C@H](N4CCOCC4)CC3)ncnc2cc1F] | 7-fluoro-6-methoxy-N-[trans-4-(morpholin-4-yl)cyclohexyl]quinazolin-4-amine | Calc'd 361.0, found 361 |
| 2-13 | 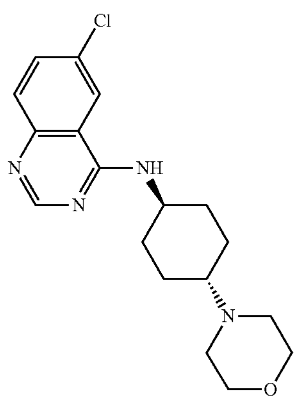 [SMILES: Clc1ccc2ncnc(N[C@H]3CC[C@H](N4CCOCC4)CC3)c2c1] | 6-chloro-N-[trans-4-(morpholin-4-yl)cyclohexyl]quinazolin-4-amine | Calc'd 347.0, found 347 |
| 2-14 | 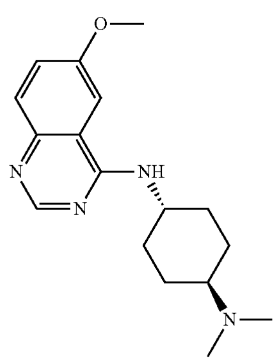 [SMILES: COc1ccc2ncnc(N[C@H]3CC[C@H](N(C)C)CC3)c2c1] | trans-N'-(6-methoxyquinazolin-4-yl)-dimethylcyclohexane-1,4-diamine | Calc'd 301.0, found 301 |
| 2-15 | 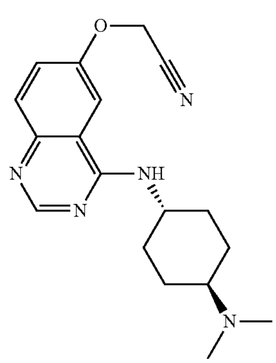 [SMILES: CN(C)[C@H]1CC[C@H](Nc2ncnc3ccc(OCC#N)cc23)CC1] | [(4-{[trans-4-(dimethylamino)cyclohexyl]amino}quinazolin-6-yl)oxy]acetonitrile | Calc'd 326.0, found 326 |

TABLE 3-continued

| Example # | Structure | Chemical Name | MS (M + 1) |
|---|---|---|---|
| 2-16 | 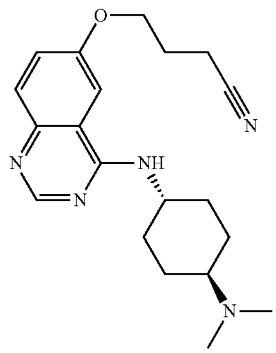 [SMILES: CN(C)[C@H]1CC[C@H](Nc2ncnc3ccc(OCCCC#N)cc23)CC1] | 4-[(4-{[trans-4-(dimethylamino)cyclohexyl]amino}quinazolin-6-yl)oxy]butanenitrile | Calc'd 354.0, found 354 |
| 2-17 | 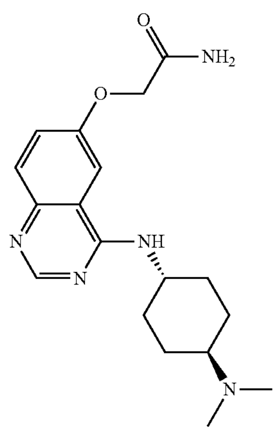 [SMILES: CN(C)[C@H]1CC[C@H](Nc2ncnc3ccc(OCC(N)=O)cc23)CC1] | 2-[(4-{[trans-4-(dimethylamino)cyclohexyl]amino}quinazolin-6-yl)oxy]acetamide | Calc'd 344.0, found 344 |
| 2-18 | 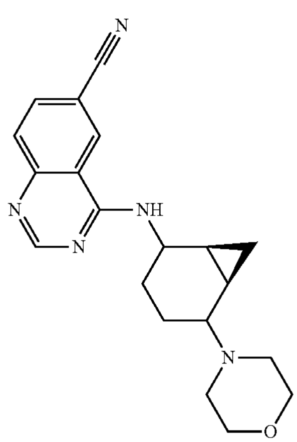 [SMILES: N#Cc1ccc2ncnc(NC3CCC(N4CCOCC4)[C@@H]4C[C@H]34)c2c1] | 4-{[(1S,6R)-5-(morpholin-4-yl)bicyclo[4.1.0]hept-2-yl]amino}quinazoline-6-carbonitrile | Calc'd 350.0, found 350 |

Example 3-1

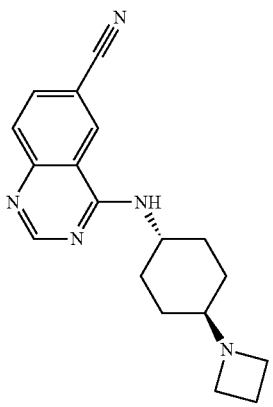 [SMILES: N#Cc1ccc2ncnc(N[C@H]3CC[C@H](N4CCC4)CC3)c2c1]

4-{[Trans-4-(azetidin-1-yl)cyclohexyl]amino}quinazoline-6-carbonitrile (Scheme 1)

4-((4-Oxocyclohexyl)amino)quinazoline-6-carbonitrile (25 mg, 0.094 mmol), azetidine (9.00 mg, 0.158 mmol), and DMF (1 mL) were added to a 2-dram vial. The vial was sealed and its contents were stirred for 6 h at 50° C. Sodium triacetoxyborohydride (29.8 mg, 0.141 mmol) was added and the resulting reaction mixture was stirred overnight at 50° C. The residue was filtered and both isomers purified by mass triggered reverse phase HPLC (ACN/water with 0.1% NH$_4$OH modifier). The desired isomer (faster eluting) was concentrated under reduced pressure to afford the title compound. MS: 308 (M+1). $^1$H NMR (600 MHz, dmso) δ 8.97 (s, 1H), 8.49 (s, 1H), 8.28 (d, J=6.5, 1H), 8.00 (d, J=8.6, 1H), 7.71 (d, J=8.5, 1H), 4.23-4.13 (m, 1H), 3.03 (s, 4H), 2.18 (s, 1H), 1.91-1.83 (m, 2H), 1.81-1.68 (m, 2H), 1.63-1.50 (m, 4H), 1.42-1.28 (m, 2H).

The following examples in Table 4 were prepared in an analogous manner to that described in Example 3-1 and general scheme 1.

TABLE 4

| Example # | Structure | Chemical Name | MS (M+1) |
|---|---|---|---|
| 3-2 | 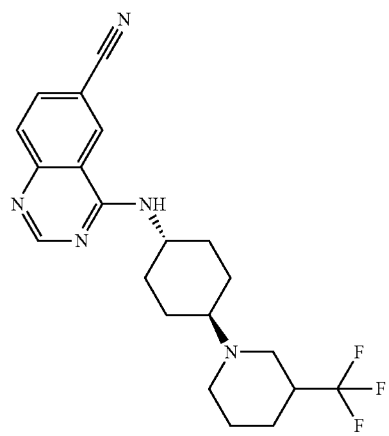 [SMILES: N#Cc1ccc2ncnc(N[C@H]3CC[C@H](N4CCCC(C(F)(F)F)C4)CC3)c2c1] | 4-({cis or trans-4-[(3R or S)-3-(trifluoromethyl)piperidin-1-yl]cyclohexyl}amino)quinazoline-6-carbonitrile | Calc'd 404.0, found 404 |
| 3-3 | 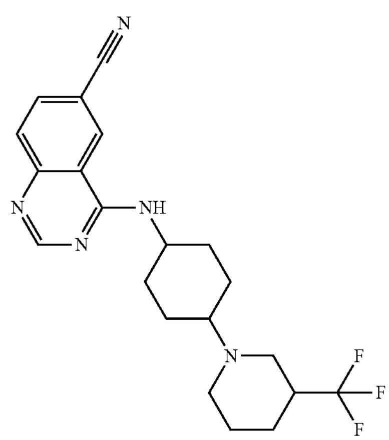 [SMILES: N#Cc1ccc2ncnc(NC3CCC(N4CCCC(C(F)(F)F)C4)CC3)c2c1] | 4-({cis or trans-4-[(3R or S)-3-(trifluoromethyl)piperidin-1-yl]cyclohexyl}amino)quinazoline-6-carbonitrile | Calc'd 404.0, found 404 |

TABLE 4-continued
| Example # | Structure | Chemical Name | MS (M+1) |
|---|---|---|---|
| 3-4 | 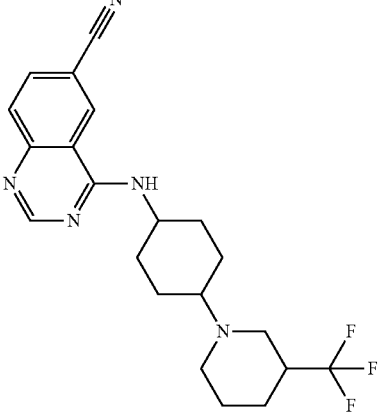 | 4-({cis or trans-4-[(3R or S)-3-(trifluoromethyl)piperidin-1-yl]cyclohexyl}amino)quinazoline-6-carbonitrile | Calc'd 404.0, found 404 |
| 3-5 | 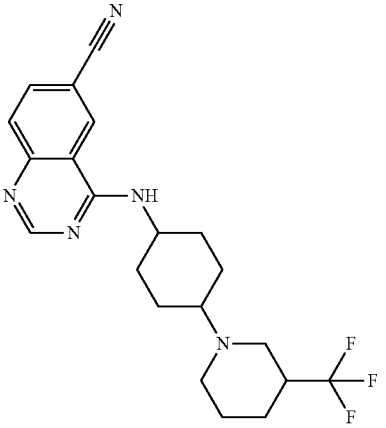 [SMILES: N#Cc1ccc2ncnc(NC3CCC(N4CCCC(C(F)(F)F)C4)CC3)c2c1] | 4-({cis or trans-4-[(3R or S)-3-(trifluoromethyl)piperidin-1-yl]cyclohexyl}amino)quinazoline-6-carbonitrile | Calc'd 404.0, found 404 |
| 3-6 | 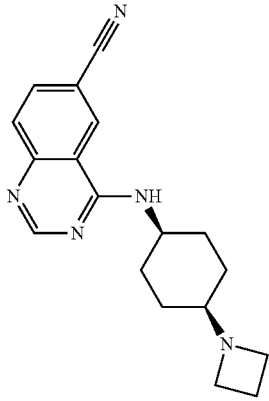 [SMILES: N#Cc1ccc2ncnc(N[C@H]3CC[C@@H](N4CCC4)CC3)c2c1] | 4-{[cis-4-(azetidin-1-yl)cyclohexyl]amino}quinazoline-6-carbonitrile | Calc'd 308.0, found 308 |

TABLE 4-continued

| Example # | Structure | Chemical Name | MS (M+1) |
|---|---|---|---|
| 3-7 | 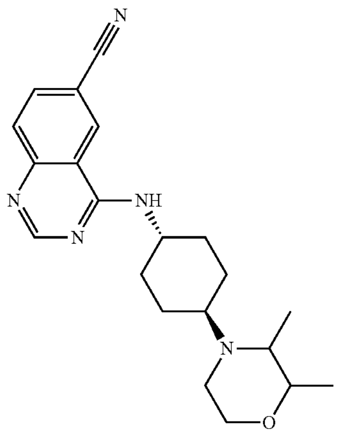 [SMILES: CC1OCCN([C@H]2CC[C@H](Nc3ncnc4ccc(C#N)cc34)CC2)C1C] | 4-{[trans-4-(2,3-dimethylmorpholin-4-yl)cyclohexyl]amino}quinazoline-6-carbonitrile | Calc'd 366.0, found 366 |
| 3-8 | 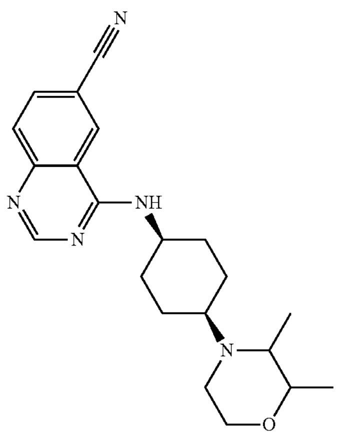 [SMILES: CC1OCCN([C@H]2CC[C@@H](Nc3ncnc4ccc(C#N)cc34)CC2)C1C] | 4-{[cis-4-(2,3-dimethylmorpholin-4-yl)cyclohexyl]amino}quinazoline-6-carbonitrile | Calc'd 366.0, found 366 |
| 3-9 | 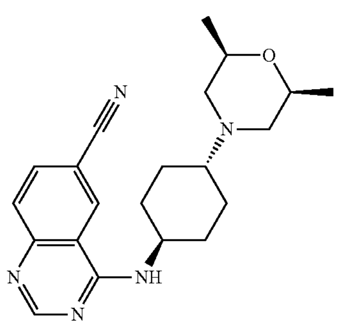 [SMILES: C[C@@H]1CN([C@H]2CC[C@H](Nc3ncnc4ccc(C#N)cc34)CC2)C[C@H](C)O1] | 4-({trans-4-[(2R,6S)-2,6-dimethylmorpholin-4-yl]cyclohexyl}amino)quinazoline-6-carbonitrile | Calc'd 366.0, found 366 |
| 3-10 | 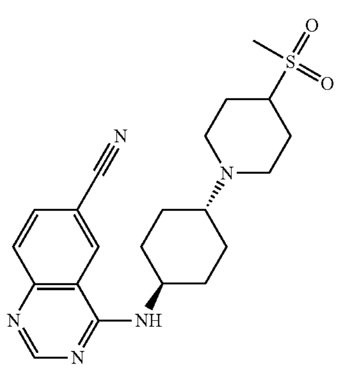 [SMILES: CS(=O)(=O)C1CCN([C@H]2CC[C@H](Nc3ncnc4ccc(C#N)cc34)CC2)CC1] | 4-({trans-4-[4-(methylsulfonyl)piperidin-1-yl]cyclohexyl}amino)quinazoline-6-carbonitrile | Calc'd 414.0, found 414 |

TABLE 4-continued

| Example # | Structure | Chemical Name | MS (M+1) |
|---|---|---|---|
| 3-11 | 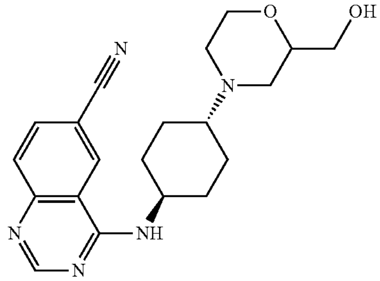 [SMILES: N#Cc1ccc2ncnc(N[C@H]3CC[C@H](N4CCOC(CO)C4)CC3)c2c1] | 4-({trans-4-[(2R or 2S)-2-(hydroxymethyl)morpholin-4-yl]cyclohexyl}amino)quinazoline-6-carbonitrile | Calc'd 368.0, found 368 |
| 3-12 | 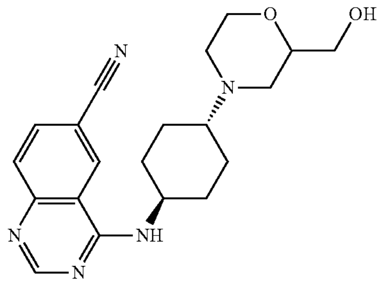 [SMILES: N#Cc1ccc2ncnc(N[C@H]3CC[C@H](N4CCOC(CO)C4)CC3)c2c1] | 4-({trans-4-[(2R or 2S)-2-(hydroxymethyl)morpholin-4-yl]cyclohexyl}amino)quinazoline-6-carbonitrile | Calc'd 368.0, found 368 |
| 3-13 | 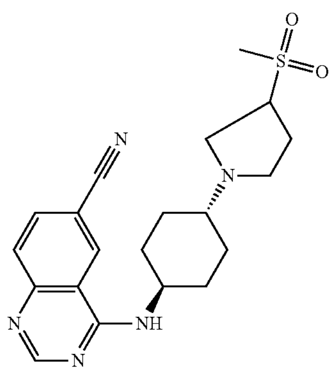 [SMILES: CS(=O)(=O)C1CCN([C@H]2CC[C@H](Nc3ncnc4ccc(C#N)cc34)CC2)C1] | 4-({trans-4-[3-(methylsulfonyl)pyrrolidin-1-yl]cyclohexyl}amino)quinazoline-6-carbonitrile | Calc'd 400.0, found 400 |
| 3-14 | 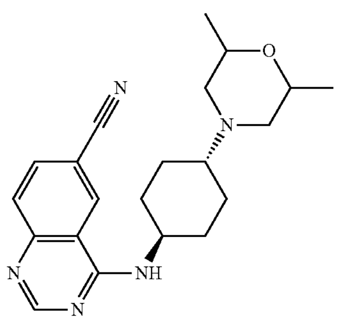 [SMILES: CC1CN([C@H]2CC[C@H](Nc3ncnc4ccc(C#N)cc34)CC2)CC(C)O1] | 4-({trans-4-[(2S,6S or 2R,6R)-2,6-dimethylmorpholin-4-yl]cyclohexyl}amino)quinazoline-6-carbonitrile | Calc'd 366.0, found 366 |
| 3-15 | 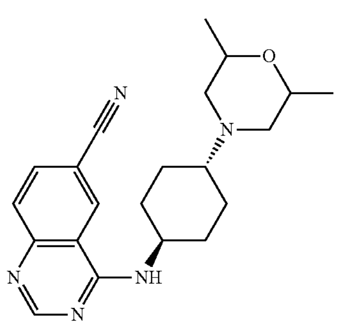 [SMILES: CC1CN([C@H]2CC[C@H](Nc3ncnc4ccc(C#N)cc34)CC2)CC(C)O1] | 4-({trans-4-[2S,6S or 2R,6R)-2,6-dimethylmorpholin-4-yl]cyclohexyl}amino)quinazoline-6-carbonitrile | Calc'd 366.0, found 366 |

TABLE 4-continued

| Example # | Structure | Chemical Name | MS (M+1) |
|---|---|---|---|
| 3-16 | 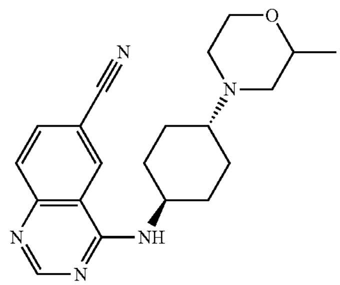 [SMILES: CC1CN([C@H]2CC[C@H](Nc3ncnc4ccc(C#N)cc34)CC2)CCO1] | 4-({trans-4-[(2S or 2R)-2-methylmorpholin-4-yl]cyclohexyl}amino)quinazoline-6-carbonitrile | Calc'd 352.0, found 352 |
| 3-17 | 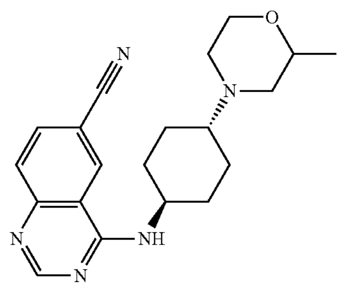 [SMILES: CC1CN([C@H]2CC[C@H](Nc3ncnc4ccc(C#N)cc34)CC2)CCO1] | 4-({trans-4-[(2S or 2R)-2-methylmorpholin-4-yl]cyclohexyl}amino)quinazoline-6-carbonitrile | Calc'd 352.0, found 352 |
| 3-18 | 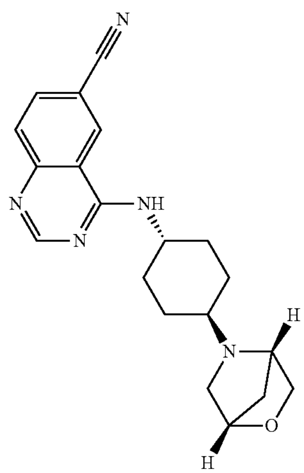 [SMILES: N#Cc1ccc2ncnc(N[C@H]3CC[C@H](N4C[C@@H]5C[C@H]4CO5)CC3)c2c1] | 4-({trans-4-[(1S,4S)-2-oxa-5-azabicyclo[2.2.1]hept-5-yl]cyclohexyl}amino)quinazoline-6-carbonitrile | Calc'd 350.0, found 350 |
| 3-19 | 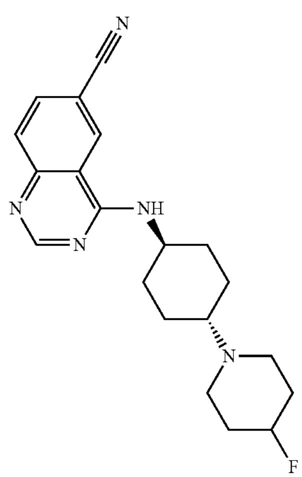 [SMILES: N#Cc1ccc2ncnc(N[C@H]3CC[C@H](N4CCC(F)CC4)CC3)c2c1] | 4-{[trans-4-(4-fluoropiperidin-1-yl)cyclohexyl]amino}quinazoline-6-carbonitrile | Calc'd 354.0, found 354 |

TABLE 4-continued

| Example # | Structure | Chemical Name | MS (M+1) |
|---|---|---|---|
| 3-20 | 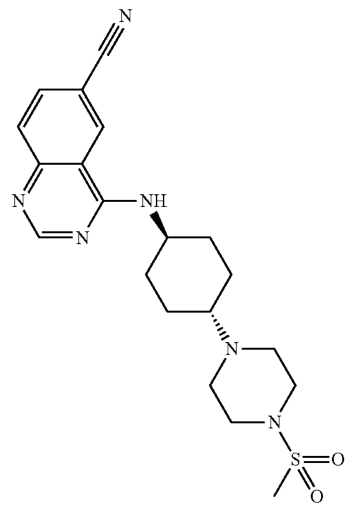 [SMILES: CS(=O)(=O)N1CCN([C@H]2CC[C@H](Nc3ncnc4ccc(C#N)cc34)CC2)CC1] | 4-({trans-4-[4-(methylsulfonyl)piperazin-1-yl]cyclohexyl}amino)quinazoline-6-carbonitrile | Calc'd 415.0, found 415 |
| 3-21 | 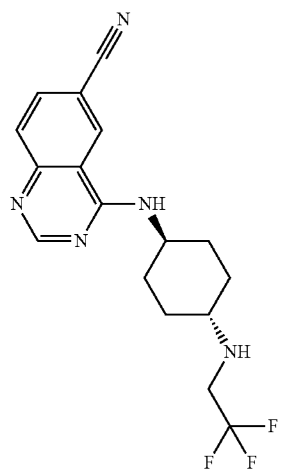 [SMILES: N#Cc1ccc2ncnc(N[C@H]3CC[C@H](NCC(F)(F)F)CC3)c2c1] | 4-({trans-4-[(2,2,2-trifluoroethyl)amino]cyclohexyl}amino)quinazoline-6-carbonitrile | Calc'd 350.0, found 350 |
| 3-22 | 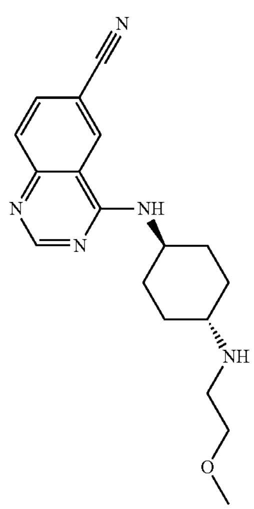 [SMILES: COCCN[C@H]1CC[C@H](Nc2ncnc3ccc(C#N)cc23)CC1] | 4-({trans-4-[(2-methoxyethyl)amino]cyclohexyl}amino)quinazoline-6-carbonitrile | Calc'd 326.0, found 326 |

TABLE 4-continued

| Example # | Structure | Chemical Name | MS (M+1) |
|---|---|---|---|
| 3-23 | 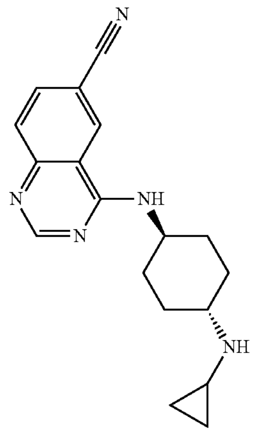 [SMILES: N#Cc1ccc2ncnc(N[C@H]3CC[C@H](NC4CC4)CC3)c2c1] | 4-{[trans-4-(cyclopropylamino)cyclohexyl]amino}quinazoline-6-carbonitrile | Calc'd 308.0, found 308 |
| 3-24 | 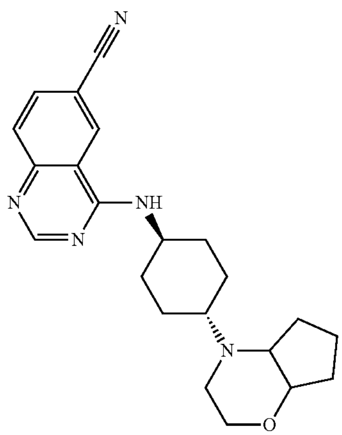 [SMILES: N#Cc1ccc2ncnc(N[C@H]3CC[C@H](N4CCOC5CCCC54)CC3)c2c1] | 4-({trans-4-[(4aS,7aS or 4aR,7aR)-hexahydrocyclopenta[b][1,4]oxazin-4(4aH)-yl]cyclohexyl}amino)quinazoline-6-carbonitrile | Calc'd 378.0, found 378 |
| 3-25 | 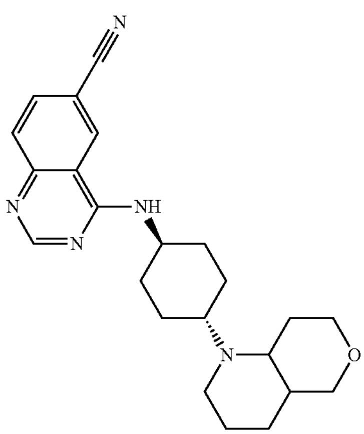 [SMILES: N#Cc1ccc2ncnc(N[C@H]3CC[C@H](N4CCCC5COCCC54)CC3)c2c1] | 4-{[trans-4-(hexahydro-2H-pyrano[4,3-b]pyridin-1(5H)-yl)cyclohexyl]amino}quinazoline-6-carbonitrile | Calc'd 392.0, found 392 |

TABLE 4-continued

| Example # | Structure | Chemical Name | MS (M+1) |
|---|---|---|---|
| 3-26 | 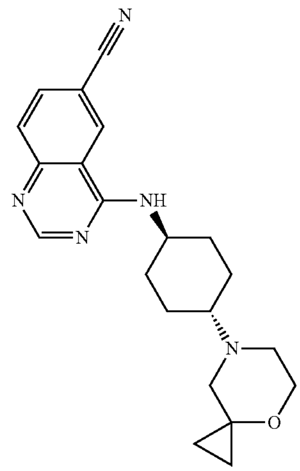 [SMILES: N#Cc1ccc2ncnc(N[C@H]3CC[C@H](N4CCOC5(CC5)C4)CC3)c2c1] | 4-{[trans-4-(4-oxa-7-azaspiro[2.5]oct-7-yl)cyclohexyl]amino}quinazoline-6-carbonitrile | Calc'd 364.0, found 364 |
| 3-27 | 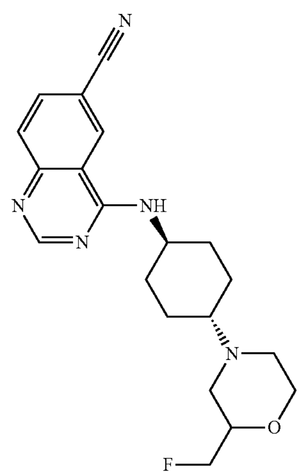 [SMILES: N#Cc1ccc2ncnc(N[C@H]3CC[C@H](N4CCOC(CF)C4)CC3)c2c1] | 4-({trans-4-[2-(fluoromethyl)morpholin-4-yl]cyclohexyl}amino)quinazoline-6-carbonitrile | Calc'd 370.0, found 370 |
| 3-28 | 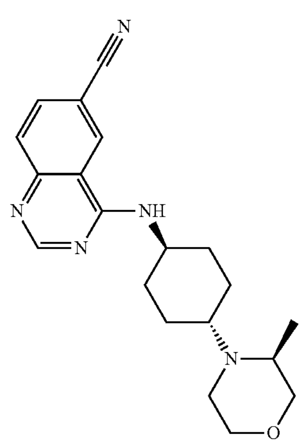 [SMILES: C[C@H]1COCCN1[C@H]1CC[C@H](Nc2ncnc3ccc(C#N)cc23)CC1] | 4-({trans-4-[(3S)-3-methylmorpholin-4-yl]cyclohexyl}amino)quinazolin-6-carbonitrile | Calc'd 352.0, found 352 |

TABLE 4-continued

| Example # | Structure | Chemical Name | MS (M+1) |
|---|---|---|---|
| 3-29 | 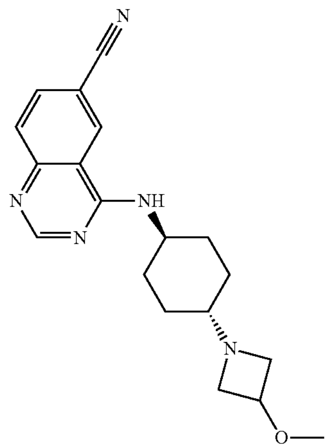 [SMILES: COC1CN([C@H]2CC[C@H](Nc3ncnc4ccc(C#N)cc34)CC2)C1] | 4-{[trans-4-(3-methoxyazetidin-1-yl)cyclohexyl]amino}quinazoline-6-carbonitrile | Calc'd 338.0, found 338 |
| 3-30 | 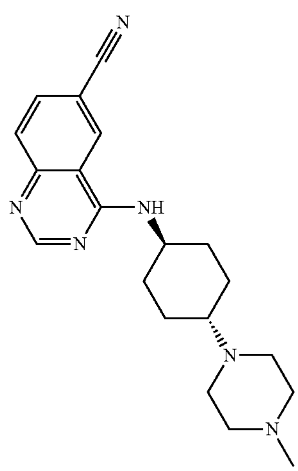 [SMILES: CN1CCN([C@H]2CC[C@H](Nc3ncnc4ccc(C#N)cc34)CC2)CC1] | 4-{[trans-4-(4-methylpiperazin-1-yl)cyclohexyl]amino}quinazoline-6-carbonitrile | Calc'd 351.0, found 351 |
| 3-31 | 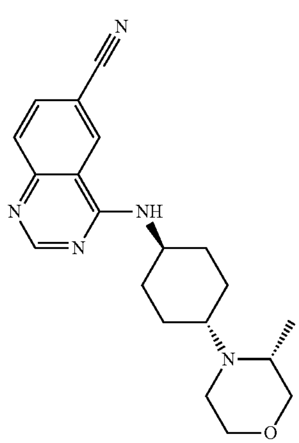 [SMILES: C[C@@H]1COCCN1[C@H]1CC[C@H](Nc2ncnc3ccc(C#N)cc23)CC1] | 4-({trans-4-[(3R)-3-methylmorpholin-4-yl]cyclohexyl}amino)quinazoline-6-carbonitrile | Calc'd 352.0, found 352 |

TABLE 4-continued
| Example # | Structure | Chemical Name | MS (M+1) |
|---|---|---|---|
| 3-32 | 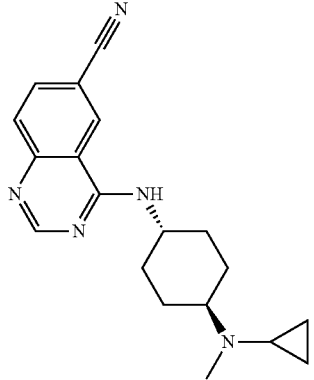 [SMILES: CN(C1CC1)[C@H]1CC[C@H](Nc2ncnc3ccc(C#N)cc23)CC1] | 4-({trans-4-[cyclopropyl(methyl)amino]cyclohexyl}amino)quinazoline-6-carbonitrile | Calc'd 322.0, found 322 |
| 3-33 | 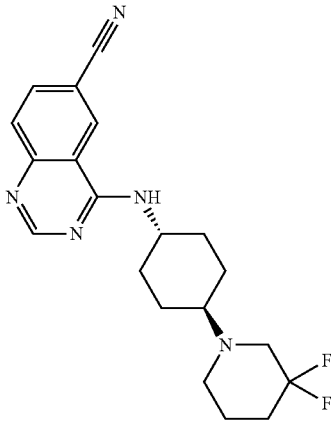 [SMILES: N#Cc1ccc2ncnc(N[C@H]3CC[C@H](N4CCCC(F)(F)C4)CC3)c2c1] | 4-{[trans-4-(3,3-difluoropiperidin-1-yl)cyclohexyl]amino}quinazoline-6-carbonitrile | Calc'd 372.0, found 372 |
| 3-34 | 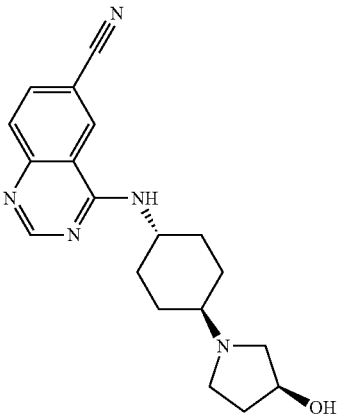 [SMILES: N#Cc1ccc2ncnc(N[C@H]3CC[C@H](N4CC[C@H](O)C4)CC3)c2c1] | 4-({trans-4-[(3S)-3-hydroxypyrrolidin-1-yl]cyclohexyl}amino)quinazoline-6-carbonitrile | Calc'd 338.0, found 338 |

| Example # | Structure | Chemical Name | MS (M+1) |
|---|---|---|---|
| 3-35 | 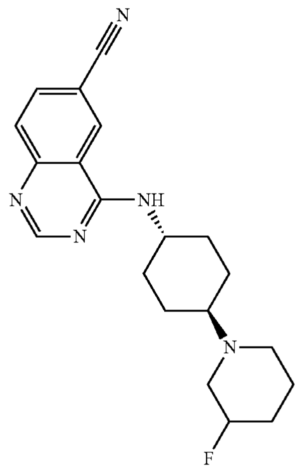 [SMILES: N#Cc1ccc2ncnc(N[C@H]3CC[C@H](N4CCCC(F)C4)CC3)c2c1] | 4-{[trans-4-(3-fluoropiperidin-1-yl)cyclohexyl]amino}quinazoline-6-carbonitrile | Calc'd 354.0, found 354 |
| 3-36 | 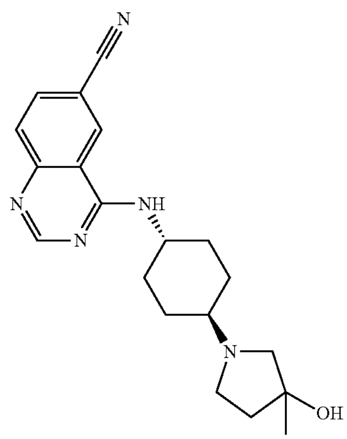 [SMILES: CC1(O)CCN([C@H]2CC[C@H](Nc3ncnc4ccc(C#N)cc34)CC2)C1] | 4-{[trans-4-(3-hydroxy-3-methylpyrrolidin-1-yl)cyclohexyl]amino}quinazoline-6-carbonitrile | Calc'd 352.0, found 352 |
| 3-37 | 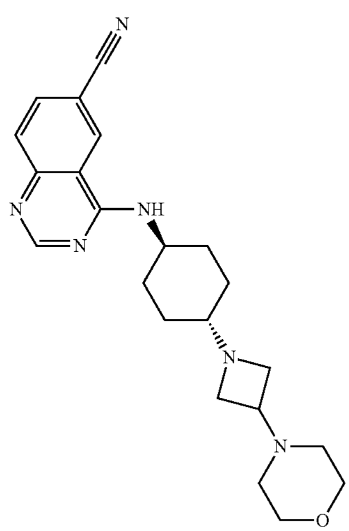 [SMILES: N#Cc1ccc2ncnc(N[C@H]3CC[C@H](N4CC(N5CCOCC5)C4)CC3)c2c1] | 4-({trans-4-[3-(morpholin-4-yl)azetidin-1-yl]cyclohexyl}amino)quinazoline-6-carbonitrile | Calc'd 393.0, found 393 |

TABLE 4-continued

| Example # | Structure | Chemical Name | MS (M+1) |
|---|---|---|---|
| 3-38 | 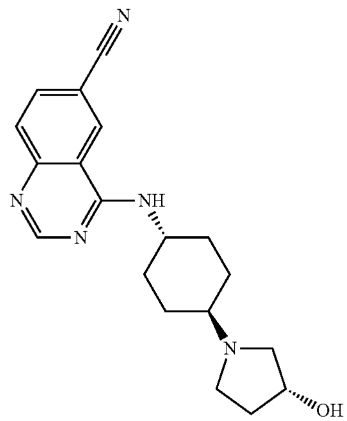 [SMILES: N#Cc1ccc2ncnc(N[C@H]3CC[C@H](N4CC[C@@H](O)C4)CC3)c2c1] | 4-({trans-4-[(3R)-3-hydroxypyrrolidin-1-yl]cyclohexyl}amino)quinazoline-6-carbonitrile | Calc'd 338.0, found 338 |
| 3-39 | 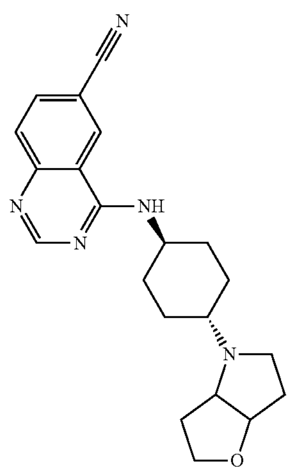 [SMILES: N#Cc1ccc2ncnc(N[C@H]3CC[C@H](N4CCC5OCCC54)CC3)c2c1] | 4-{[trans-4-(hexahydro-4H-furo[3,2-b]pyrrol-4-yl)cyclohexyl]amino}quinazoline-6-carbonitrile | Calc'd 364.0, found 364 |
| 3-40 | 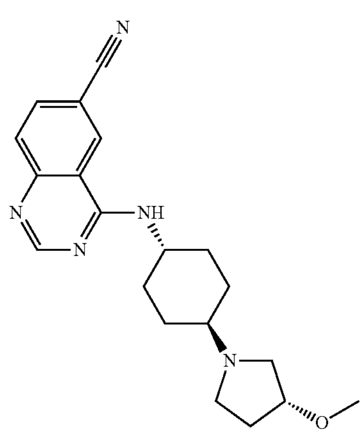 [SMILES: CO[C@@H]1CCN([C@H]2CC[C@H](Nc3ncnc4ccc(C#N)cc34)CC2)C1] | 4-({trans-4-[(3R)-3-methoxypyrrolidin-1-yl]cyclohexyl}amino)quinazoline-6-carbonitrile | Calc'd 352.0, found 352 |

TABLE 4-continued
| Example # | Structure | Chemical Name | MS (M+1) |
|---|---|---|---|
| 3-41 | 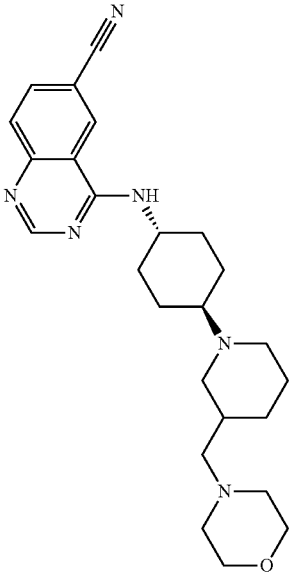 [SMILES: N#Cc1ccc2ncnc(N[C@H]3CC[C@H](N4CCCC(CN5CCOCC5)C4)CC3)c2c1] | 4-({trans-4-[(3R or 3S)-3-(morpholin-4-ylmethyl)piperidin-1-yl]cyclohexyl}amino)quinazoline-6-carbonitrile | Calc'd 435.0, found 435 |
| 3-42 | 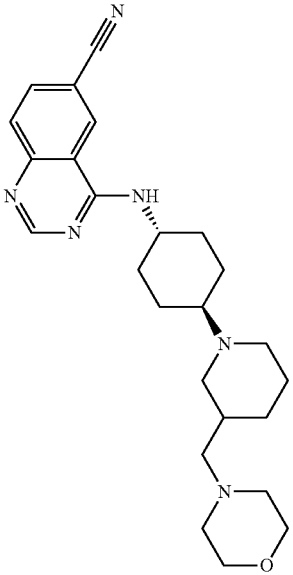 [SMILES: N#Cc1ccc2ncnc(N[C@H]3CC[C@H](N4CCCC(CN5CCOCC5)C4)CC3)c2c1] | 4-({trans-4-[(3R or 3S)-3-(morpholin-4-ylmethyl)piperidin-1-yl]cyclohexyl}amino)quinazoline-6-carbonitrile | Calc'd 435.0, found 435 |

TABLE 4-continued

| Example # | Structure | Chemical Name | MS (M+1) |
|---|---|---|---|
| 3-43 | 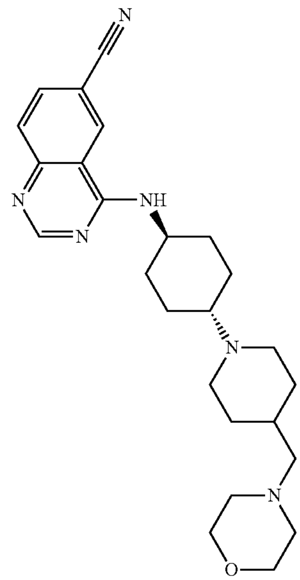 [SMILES: N#Cc1ccc2ncnc(N[C@H]3CC[C@H](N4CCC(CN5CCOCC5)CC4)CC3)c2c1] | 4-({trans-4-[4-(mopholin-4-ylmethyl)piperidin-1-yl]cyclohexyl}amino)quinazoline-6-carbonitrile | Calc'd 435.0, found 435 |
| 3-44 | 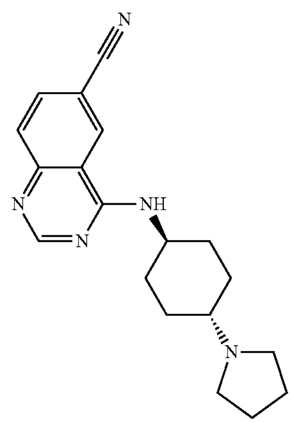 [SMILES: N#Cc1ccc2ncnc(N[C@H]3CC[C@H](N4CCCC4)CC3)c2c1] | 4-{[trans-4-(pyrrolidin-1-yl)cyclohexyl]amino}quinazoline-6-carbonitrile | Calc'd 322.0, found 322 |
| 3-45 | 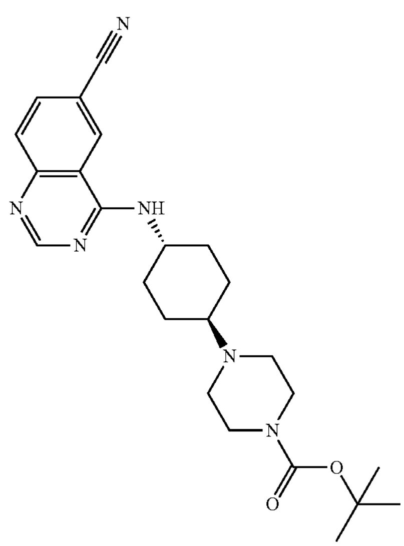 [SMILES: CC(C)(C)OC(=O)N1CCN([C@H]2CC[C@H](Nc3ncnc4ccc(C#N)cc34)CC2)CC1] | tert-butyl 4-{trans-4-[(6-cyanoquinazolin-4-yl)amino]cyclohexyl}piperazine-1-carboxylate | Calc'd 437.0, found 437 |

TABLE 4-continued

| Example # | Structure | Chemical Name | MS (M+1) |
|---|---|---|---|
| 3-46 | 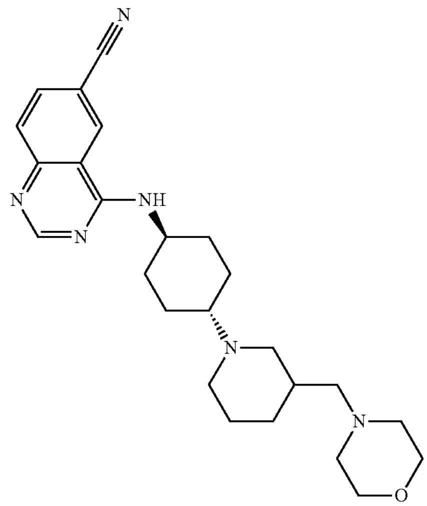 [SMILES: N#Cc1ccc2ncnc(N[C@H]3CC[C@H](N4CCCC(CN5CCOCC5)C4)CC3)c2c1] | 4-({trans-4-[3-(morpholin-4-ylmethyl)piperidin-1-yl]cyclohexyl}amino)quinazoline-6-carbonitrile | Calc'd 435.0, found 435 |
| 3-47 | 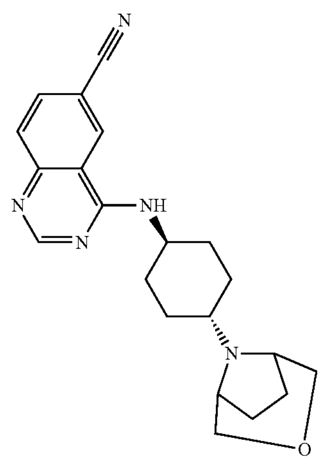 [SMILES: N#Cc1ccc2ncnc(N[C@H]3CC[C@H](N4C5CCC4COC5)CC3)c2c1] | 4-{[trans-4-(3-oxa-8-azabicyclo[3.2.1]oct-8-yl)cyclohexyl]amino}quinazoline-6-carbonitrile | Calc'd 364.0, found 364 |
| 3-48 | 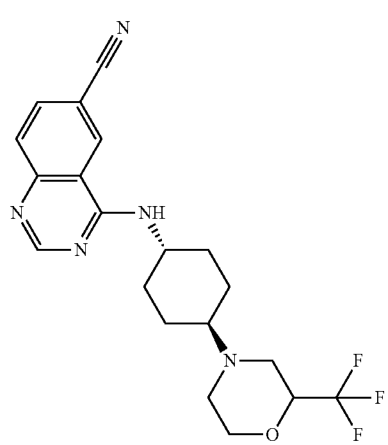 [SMILES: N#Cc1ccc2ncnc(N[C@H]3CC[C@H](N4CCOC(C(F)(F)F)C4)CC3)c2c1] | 4-({trans-4-[(2R or 2S)-2-(trifluoromethyl)morpholin-4-yl]cyclohexyl}amino)quinazoline-6-carbonitrile | Calc'd 406.0, found 406 |

TABLE 4-continued
| Example # | Structure | Chemical Name | MS (M+1) |
|---|---|---|---|
| 3-49 | 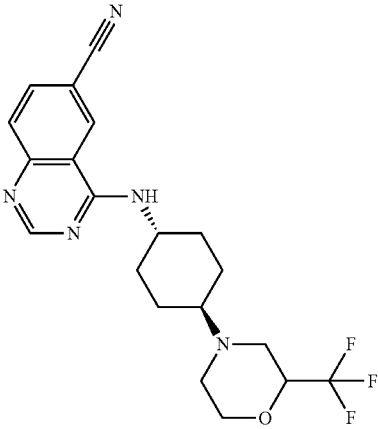 | 4-({trans-4-[(2R or 2S)-2-(trifluoromethyl)morpholin-4-yl]cyclohexyl}amino)quinazoline-6-carbonitrile | Calc'd 406.0, found 406 |
| 3-50 | 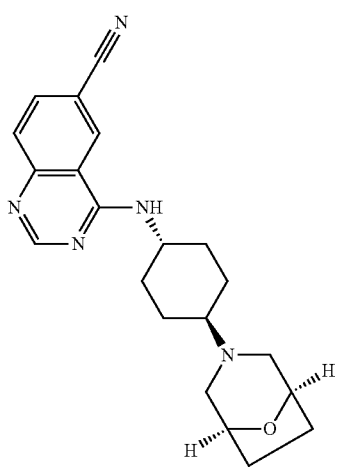 [SMILES: N#Cc1ccc2ncnc(N[C@H]3CC[C@H](N4C[C@H]5CC[C@@H](C4)O5)CC3)c2c1] | 4-({trans-4-[(1R,5S)-8-oxa-3-azabicylco[3.2.1]oct-3-yl]cyclohexyl}amino)quinazoline-6-carbonitrile | Calc'd 364.0, found 364 |
| 3-51 | 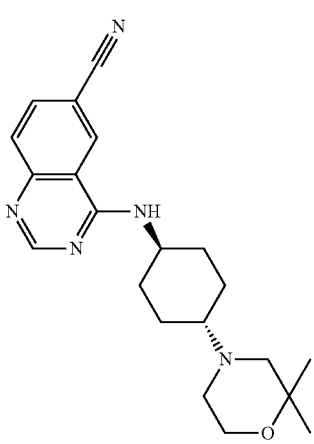 [SMILES: CC1(C)CN([C@H]2CC[C@H](Nc3ncnc4ccc(C#N)cc34)CC2)CCO1] | 4-{[trans-4-(2,2-dimethylmorpholin-4-yl)cyclohexyl]amino}quinazoline-6-carbonitrile | Calc'd 366.0, found 366 |

TABLE 4-continued

| Example # | Structure | Chemical Name | MS (M+1) |
|---|---|---|---|
| 3-52 | 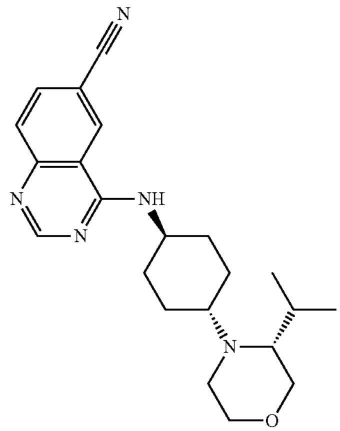 [SMILES: CC(C)[C@@H]1COCCN1[C@H]1CC[C@H](Nc2ncnc3ccc(C#N)cc23)CC1] | 4-({trans-4-[(3R)-3-(propan-2-yl)morpholin-4-yl]cyclohexyl}amino)quinazoline-6-carbonitrile | Calc'd 380.0, found 380 |
| 3-53 | 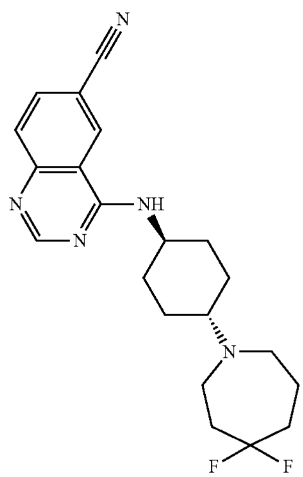 [SMILES: N#Cc1ccc2ncnc(N[C@H]3CC[C@H](N4CCCC(F)(F)CC4)CC3)c2c1] | 4-{[trans-4-(4,4-difluoroazepan-1-yl)cyclohexyl]amino}quinazoline-6-carbonitrile | Calc'd 386.0, found 386 |
| 3-54 | 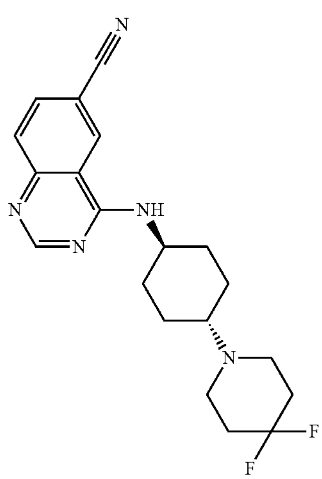 [SMILES: N#Cc1ccc2ncnc(N[C@H]3CC[C@H](N4CCC(F)(F)CC4)CC3)c2c1] | 4-{[trans-4-(4,4-difluoropiperidin-1-yl)cyclohexyl]amino}quinazoline-6-carbonitrile | Calc'd 372.0, found 372 |

TABLE 4-continued

| Example # | Structure | Chemical Name | MS (M+1) |
|---|---|---|---|
| 3-55 | 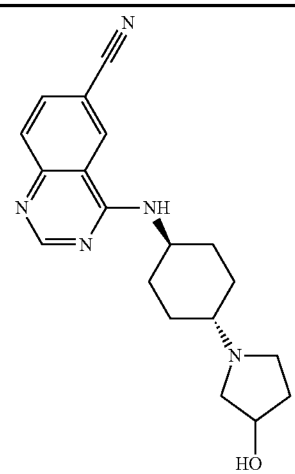 | 4-{[trans-4-(3-hydroxypyrrolidin-1-yl)cyclohexyl]amino}quinazoline-6-carbonitrile | Calc'd 338.0, found 338 |

Example 4-1

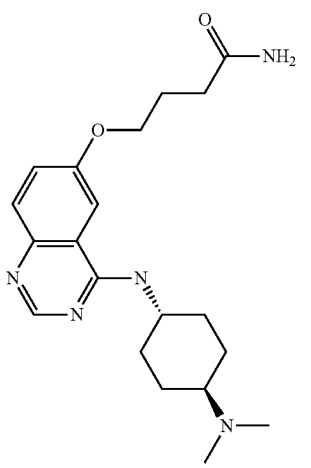 [SMILES: CN(C)[C@H]1CC[C@H](Nc2ncnc3ccc(OCCCC(N)=O)cc23)CC1]

4-[(4-{[Trans-4-(dimethylamino)cyclohexyl]amino}quinazolin-6-yl)oxy]butanamide (Scheme 3)

Aqueous hydrogen peroxide (30%, 0.142 mL, 1.42 mmol) was added dropwise to a solution of 4-((4-(((trans)-4-(dimethylamino)cyclohexyl)amino)quinazolin-6-yl)oxy)butanenitrile (0.05 g, 0.14 mmol) in aqueous ammonium hydroxide (0.2 M, 7.07 mL, 1.42 mmol). The reaction was stirred for 18 h at rt. The reaction was filtered, and the solvent removed under reduced pressure. The material was purified by mass triggered reverse phase HPLC (ACN/water with 0.1% TFA modifier) to afford the title compound as the TFA salt. MS: 372 (M+1). $^1$H NMR (600 MHz, dmso) δ 9.67 (s, 1H), 9.57 (d, J=7.3, 1H), 8.81 (s, 1H), 7.93 (d, J=2.4, 1H), 7.74 (d, J=9.1, 1H), 7.65 (dd, J=2.4, 9.1, 1H), 7.33 (s, 1H), 6.79 (s, 1H), 4.42-4.32 (m, 1H), 4.10 (t, J=6.2, 2H), 3.27-3.17 (m, 1H), 2.75 (s, 3H), 2.74 (s, 3H), 2.24 (t, J=7.2, 2H), 2.12-2.04 (m, J=9.3, 4H), 2.01-1.93 (m, J=6.8, 2H), 1.68-1.51 (m, 4H).

Example 5-1

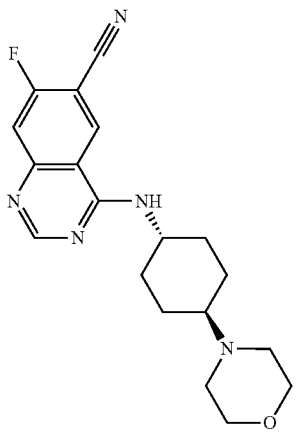 [SMILES: N#Cc1cc2c(N[C@H]3CC[C@H](N4CCOCC4)CC3)ncnc2cc1F]

7-Fluoro-4-{[trans-4-(morpholin-4-yl)cyclohexyl]amino}quinazoline-6-carbonitrile (Scheme 4)

Tetrakis(triphenylphosphine)palladium (19.8 mg, 0.017 mmol), zinc cyanide (15.06 mg, 0.128 mmol), 6-bromo-7-fluoro-N-((trans)-4-morpholinocyclohexyl)quinazolin-4-amine (35 mg, 0.086 mmol) and DMA (800 μl) were added to a microwave vial. The reaction mixture was stirred at 70° C. for 16 h. Additional tetrakis(triphenylphosphine)palladium (19.8 mg, 0.017 mmol) was added, and the reaction mixture was heated to 150° C. for 10 minutes in a microwave reactor. The mixture was filtered and purified by mass triggered reverse phase HPLC (ACN/water with 0.1% TFA modifier) to afford the title compound as the TFA salt. MS: 356 (M+1). $^1$H NMR (600 MHz, DMSO-d$_6$) δ 9.01 (d, J=7.0, 1H), 8.50 (s, 1H), 8.32 (d, J=7.4, 1H), 7.61 (d, J=10.8, 1H), 4.12-4.04 (m, 1H), 3.55-3.50 (m, 4H), 2.46-2.42 (m, 4H), 2.25-2.18 (m, 1H), 2.02-1.96 (m, 2H), 1.89-1.83 (m, 2H), 1.42-1.26 (m, 4H).

The following example in Table 5 was prepared in an analogous manner to that described in Example 5-1 and general scheme 4.

TABLE 5

| Example # | Structure | Chemical Name | MS (M+1) |
|---|---|---|---|
| 5-2 | 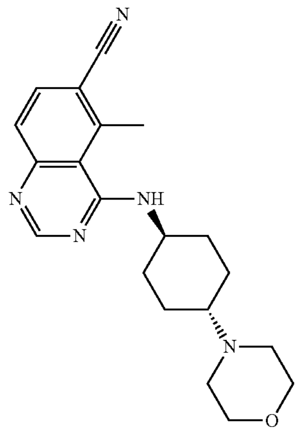 [SMILES: Cc1c(C#N)ccc2ncnc(N[C@H]3CC[C@H](N4CCOCC4)CC3)c12] | 5-methyl-4-{[trans-4-(morpholin-4-yl)cyclohexyl]amino}quinazoline-6-carbonitrile | Calc'd 352.0, found 352 |

Example 6-1

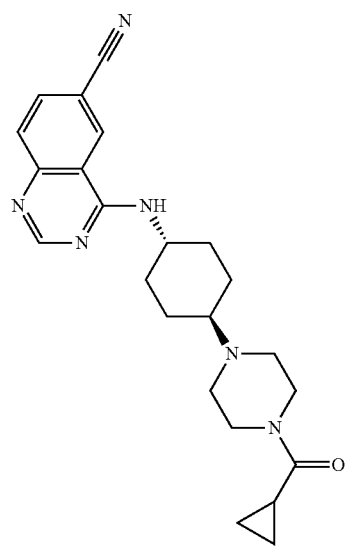 [SMILES: N#Cc1ccc2ncnc(N[C@H]3CC[C@H](N4CCN(C(=O)C5CC5)CC4)CC3)c2c1]

4-({Trans-4-[4-(cyclopropylcarbonyl)piperazin-1-yl]cyclohexyl}amino)quinazoline-6-carbonitrile
(Scheme 6)

Step 1: 4-{[Trans-4-(piperazin-1-yl)cyclohexyl]amino}quinazoline-6-carbonitrile, 2HCl A solution of tert-butyl 4-{trans-4-[(6-cyanoquinazolin-4-yl)amino]cyclohexyl}piperazine-1-carboxylate (517 mg, 1.18 mmol) in Methanol (10.0 mL) was added to a a 100 mL round bottom flask. HCl (4M in Dioxane) (10.0 mL, 40.0 mmol) was added, the flask was sealed and its contents were allowed to stir for 4 hours at room temperature. The reaction mixture was concentrated under reduced pressure to afford the title product as a dihydrochloride salt. MS: 337 (M+1).

Step 2: 4-({Trans-4-[4-(cyclopropylcarbonyl)piperazin-1-yl]cyclohexyl}amino)quinazoline-6-carbonitrile A solution of 4-{[trans-4-(piperazin-1-yl)cyclohexyl]amino}quinazoline-6-carbonitrile, 2HCl (11.0 mg, 0.029 mmol), cyclopropanecarboxylic acid (2.54 mg, 0.029 mmol), and HATU (16.8 mg, 0.044 mmol) in DMF (0.50 mL) were added to a vial. DIEA (0.015 mL, 0.088 mmol) was added, the vial was sealed and its contents were allowed to react for 30 minutes at room temperature. The mixture was filtered and purified by mass triggered reverse phase HPLC (ACN/water with 0.1% NH$_4$OH modifier) to afford the title compound. MS: 405 (M+1). $^1$H NMR (600 MHz, DMSO-d$_6$): δ 8.90 (d; J=1.74 Hz; 1H); 8.51 (s; 1H); 8.24 (d; J=7.53 Hz; 1H); 8.02 (dd; J=8.63; 1.73 Hz; 1H); 7.72 (d; J=8.63 Hz; 1H); 4.08-4.12 (m; 1H); 3.61 (s; 2H); 3.40 (s; 2H); 2.51 (s; 2H); 2.43 (s; 2H); 2.32-2.35 (m; 1H); 1.99-2.01 (m; 2H); 1.90-1.94 (m; 1H); 1.82-1.84 (m; 2H); 1.31-1.43 (m; 4H); 0.63-0.69 (m; 4H).

The following examples in Table 6 were prepared in an analogous manner to that described in Example 6-1 and general scheme 6.

TABLE 6

| Example # | Structure | Chemical Name | MS (M+1) |
|---|---|---|---|
| 6-2 | 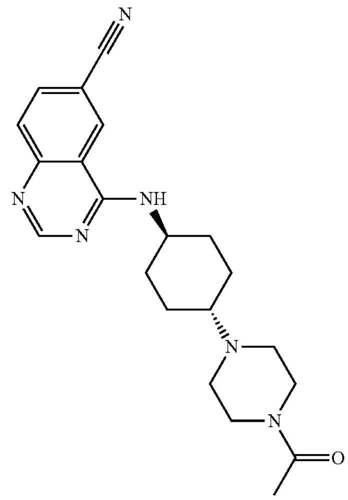 [SMILES: CC(=O)N1CCN([C@H]2CC[C@H](Nc3ncnc4ccc(C#N)cc34)CC2)CC1] | 4-{[trans-4-(4-acetylpiperazin-1-yl)cyclohexyl]amino}quinazoline-6-carbonitrile | Calc'd 379.0, found 379 |
| 6-3 | 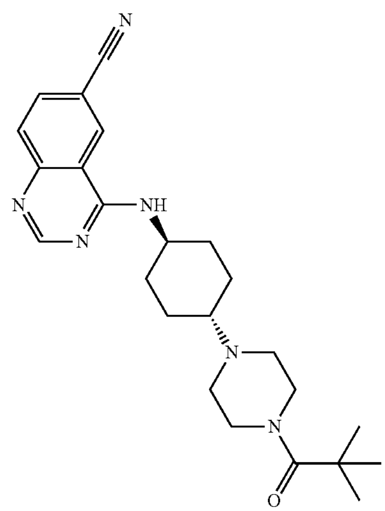 [SMILES: CC(C)(C)C(=O)N1CCN([C@H]2CC[C@H](Nc3ncnc4ccc(C#N)cc34)CC2)CC1] | 4-({trans-4-[4-(2,2-dimethylpropanoyl)piperazin-1-yl]cyclohexyl}amino)quinazoline-6-carbonitrile | Calc'd 421.0, found 421 |
| 6-4 | 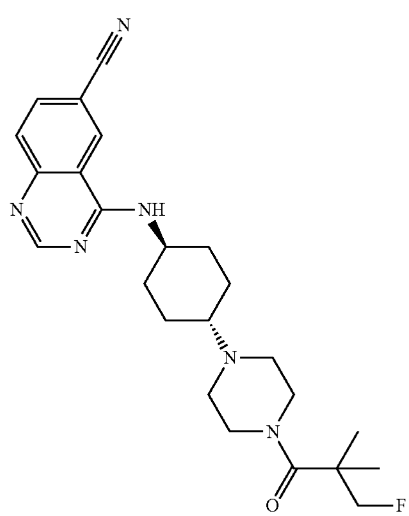 [SMILES: CC(C)(CF)C(=O)N1CCN([C@H]2CC[C@H](Nc3ncnc4ccc(C#N)cc34)CC2)CC1] | 4-({trans-4-[4-(3-fluoro-2,2-dimethylpropanoyl)piperazin-1-yl]cyclohexyl}amino)quinazoline-6-carbonitrile | Calc'd 439.0, found 439 |

TABLE 6-continued

| Example # | Structure | Chemical Name | MS (M+1) |
|---|---|---|---|
| 6-5 | 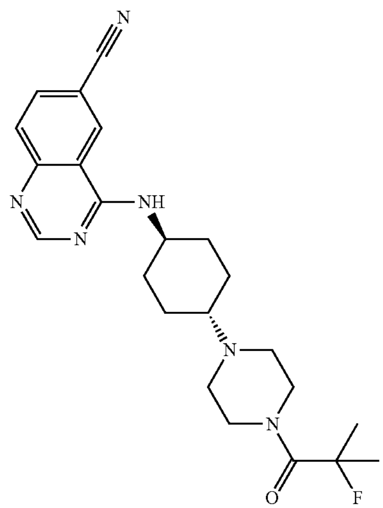 [SMILES: CC(C)(F)C(=O)N1CCN([C@H]2CC[C@H](Nc3ncnc4ccc(C#N)cc34)CC2)CC1] | 4-({trans-4-[4-(2-fluoro-2-methylpropanoyl)piperazin-1-yl]cyclohexyl}amino)quinazoline-6-carbonitrile | Calc'd 425.0, found 425 |
| 6-6 | 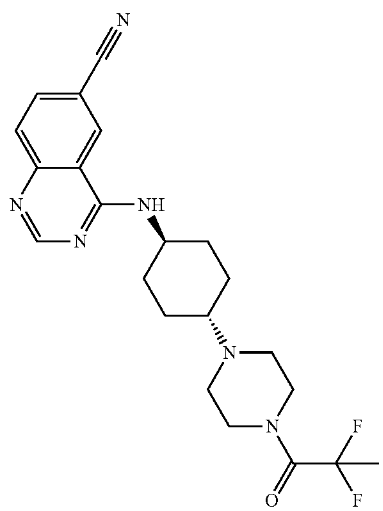 [SMILES: CC(F)(F)C(=O)N1CCN([C@H]2CC[C@H](Nc3ncnc4ccc(C#N)cc34)CC2)CC1] | 4-({trans-4-[4-(2,2-difluoropropanoyl)piperazin-1-yl]cyclohexyl}amino)quinazoline-6-carbonitrile | Calc'd 429.0, found 429 |
| 6-7 | 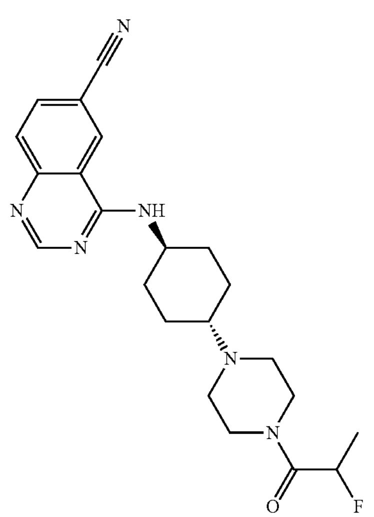 [SMILES: CC(F)C(=O)N1CCN([C@H]2CC[C@H](Nc3ncnc4ccc(C#N)cc34)CC2)CC1] | 4-({trans-4-[4-(2-fluoropropanoyl)piperazin-1-yl]cyclohexyl}amino)quinazoline-6-carbonitrile | Calc'd 411.0, found 411 |

TABLE 6-continued

| Example # | Structure | Chemical Name | MS (M+1) |
|---|---|---|---|
| 6-8 | 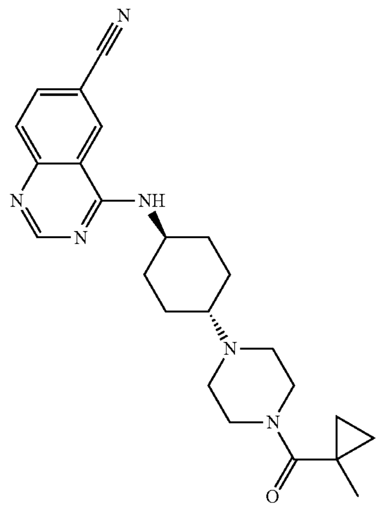 [SMILES: CC1(C(=O)N2CCN([C@H]3CC[C@H](Nc4ncnc5ccc(C#N)cc45)CC3)CC2)CC1] | 4-[(trans-4-{4-[(1-methylcyclopropyl)carbonyl]piperazin-1-yl}cyclohexyl)amino]quinazoline-6-carbonitrile | Calc'd 419.0, found 419 |
| 6-9 | 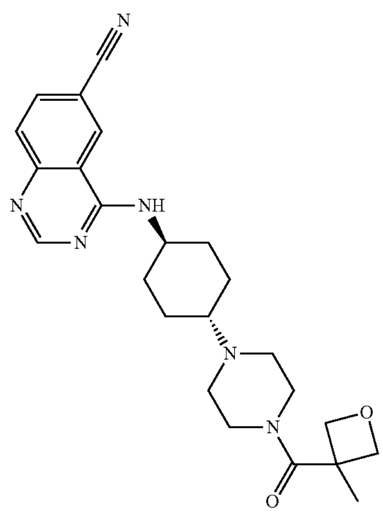 [SMILES: CC1(C(=O)N2CCN([C@H]3CC[C@H](Nc4ncnc5ccc(C#N)cc45)CC3)CC2)COC1] | 4-[(trans-4-{4-[(3-methyloxetan-3-yl)carbonyl]piperazin-1-yl}cyclohexyl)amino]quinazoline-6-carbonitrile | Calc'd 435.0, found 435 |
| 6-10 | 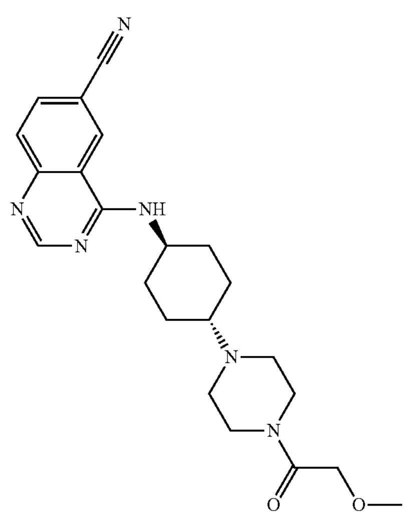 [SMILES: COCC(=O)N1CCN([C@H]2CC[C@H](Nc3ncnc4ccc(C#N)cc34)CC2)CC1] | 4-({trans-4-[4-(methoxyacetyl)piperazin-1-yl]cyclohexyl}amino)quinazoline-6-carbonitrile | Calc'd 409.0, found 409 |

TABLE 6-continued

| Example # | Structure | Chemical Name | MS (M+1) |
|---|---|---|---|
| 6-11 | 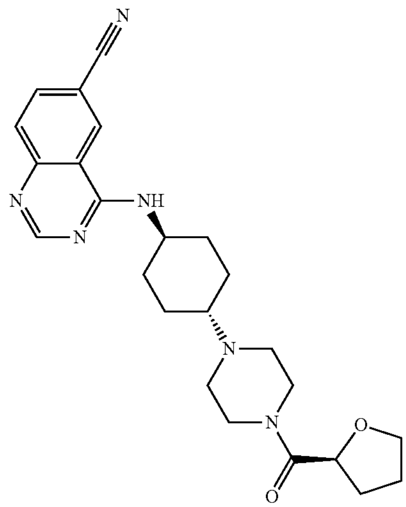 [SMILES: N#Cc1ccc2ncnc(N[C@H]3CC[C@H](N4CCN(C(=O)[C@@H]5CCCO5)CC4)CC3)c2c1] | 4-[(trans-4-{4-[(2S)-tetrahydrofuran-2-ylcarbonyl]piperazin-1-yl}cyclohexyl)amino]quinazoline-6-carbonitrile | Calc'd 435.0, found 435 |
| 6-12 | 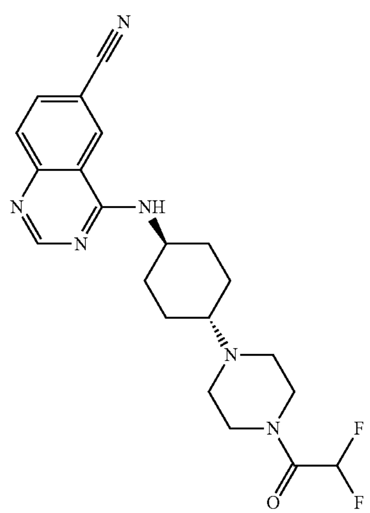 | 4-({trans-4-[4-(difluoroacetyl)piperazin-1-yl]cyclohexyl}amino)quinazoline-6-carbonitrile | Calc'd 415.0, found 415 |
| 6-13 | 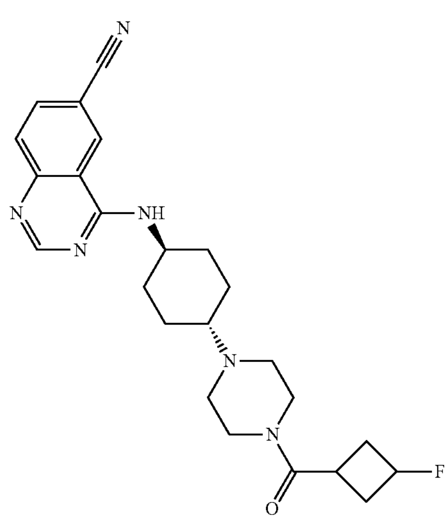 [SMILES: N#Cc1ccc2ncnc(N[C@H]3CC[C@H](N4CCN(C(=O)C5CC(F)C5)CC4)CC3)c2c1] | 4-[(trans-4-{4-[(3-fluorocyclobutyl)carbonyl]piperazin-1-yl}cyclohexyl)amino]quinazoline-6-carbonitrile | Calc'd 437.0, found 437 |

TABLE 6-continued

| Example # | Structure | Chemical Name | MS (M+1) |
|---|---|---|---|
| 6-14 | 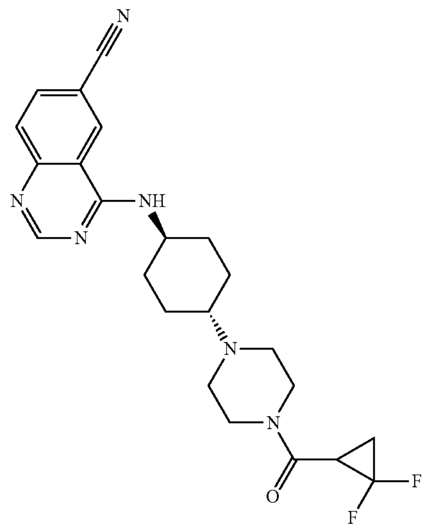 [SMILES: N#Cc1ccc2ncnc(N[C@H]3CC[C@H](N4CCN(C(=O)C5CC5(F)F)CC4)CC3)c2c1] | 4-[(trans-4-{4-[(2,2-difluorocyclopropyl)carbonyl]piperazin-1-yl}cyclohexyl)amino]quinazoline-6-carbonitrile | Calc'd 441.0, found 441 |
| 6-15 | 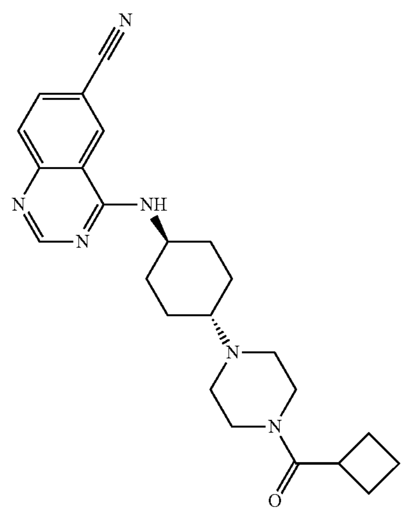 [SMILES: N#Cc1ccc2ncnc(N[C@H]3CC[C@H](N4CCN(C(=O)C5CCC5)CC4)CC3)c2c1] | 4-({trans-4-[4-(cyclobutylcarbonyl)piperazin-1-yl]cyclohexyl}amino)quinazoline-6-carbonitrile | Calc'd 419.0, found 419 |
| 6-16 | 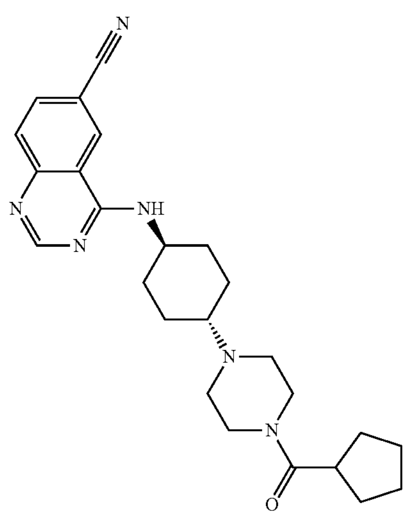 | 4-({trans-4-[4-(cyclopentylcarbonyl)piperazin-1-yl]cyclohexyl}amino)quinazoline-6-carbonitrile | Calc'd 433.0, found 433 |

TABLE 6-continued

| Example # | Structure | Chemical Name | MS (M+1) |
|---|---|---|---|
| 6-17 | 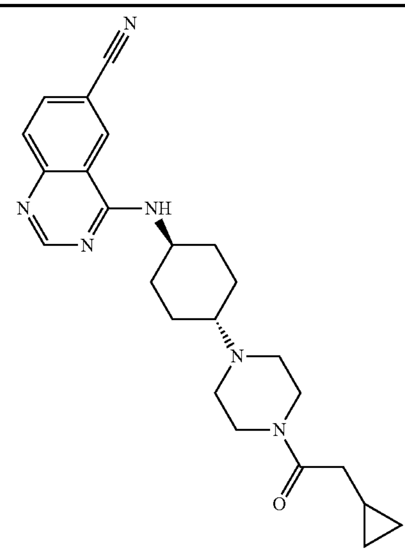 | 4-({trans-4-[4-(cyclopropylacetyl)piperazin-1-yl]cyclohexyl}amino)quinazoline-6-carbonitrile | Calc'd 419.0, found 419 |
| 6-18 | 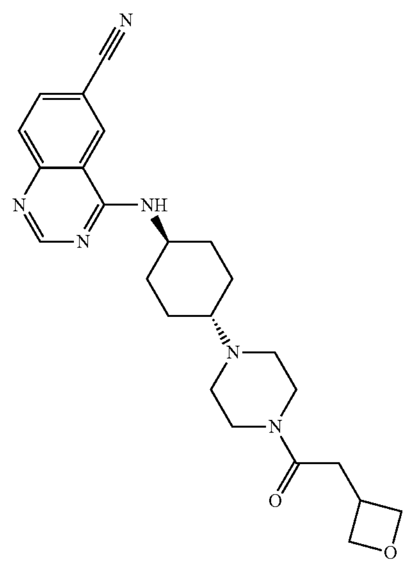 [SMILES: N#Cc1ccc2ncnc(N[C@H]3CC[C@H](N4CCN(C(=O)CC5COC5)CC4)CC3)c2c1] | 4-({trans-4-[4-(oxetan-3-ylacetyl)piperazin-1-yl]cyclohexyl}amino)quinazoline-6-carbonitrile | Calc'd 435.0, found 435 |
| 6-19 | 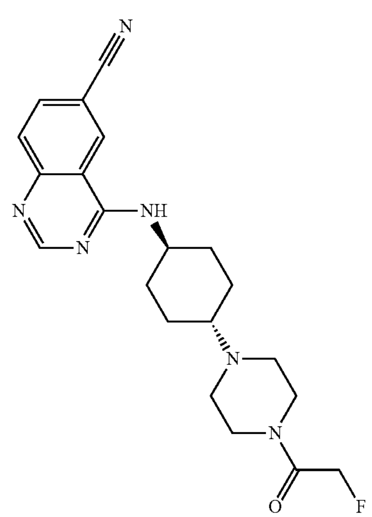 [SMILES: N#Cc1ccc2ncnc(N[C@H]3CC[C@H](N4CCN(C(=O)CF)CC4)CC3)c2c1] | 4-({trans-4-[4-(fluoroacetyl)piperazin-1-yl]cyclohexyl}amino)quinazoline-6-carbonitrile | Calc'd 397.0, found 397 |

TABLE 6-continued

| Example # | Structure | Chemical Name | MS (M+1) |
|---|---|---|---|
| 6-20 | 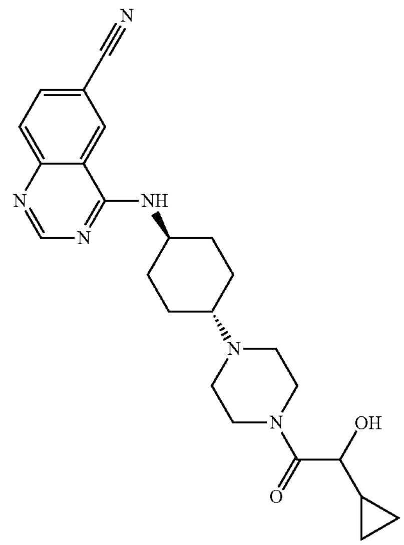 [SMILES: N#Cc1ccc2ncnc(N[C@H]3CC[C@H](N4CCN(C(=O)C(O)C5CC5)CC4)CC3)c2c1] | 4-[(trans-4-{4-[cyclopropyl(hydroxy)acetyl]piperazin-1-yl}cyclohexyl)amino]quinazoline-6-carbonitrile | Calc'd 435.0, found 435 |
| 6-21 | 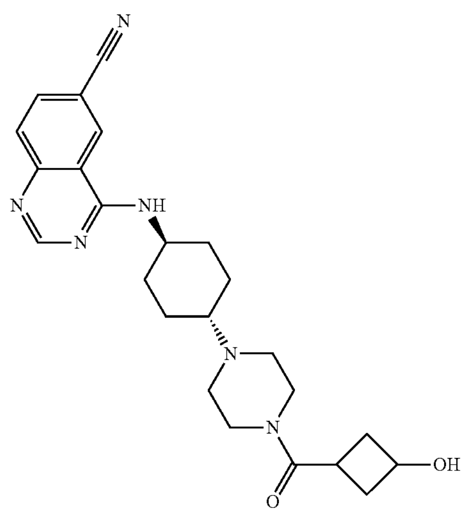 [SMILES: N#Cc1ccc2ncnc(N[C@H]3CC[C@H](N4CCN(C(=O)C5CC(O)C5)CC4)CC3)c2c1] | 4-[(trans-4-{4-[(3-hydroxycyclobutyl)carbonyl]piperazin-1-yl}cyclohexyl)amino]quinazoline-6-carbonitrile | Calc'd 435.0, found 435 |
| 6-22 | 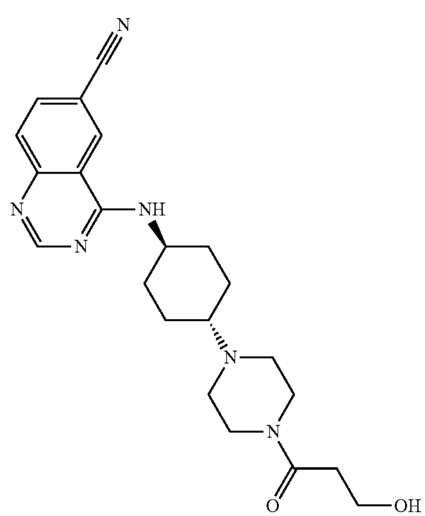 [SMILES: N#Cc1ccc2ncnc(N[C@H]3CC[C@H](N4CCN(C(=O)CCO)CC4)CC3)c2c1] | 4-({trans-4-[4-(3-hydroxypropanoyl)piperazin-1-yl]cyclohexyl}amino)quinazoline-6-carbonitrile | Calc'd 409.0, found 409 |

TABLE 6-continued

| Example # | Structure | Chemical Name | MS (M+1) |
| --- | --- | --- | --- |
| 6-23 | 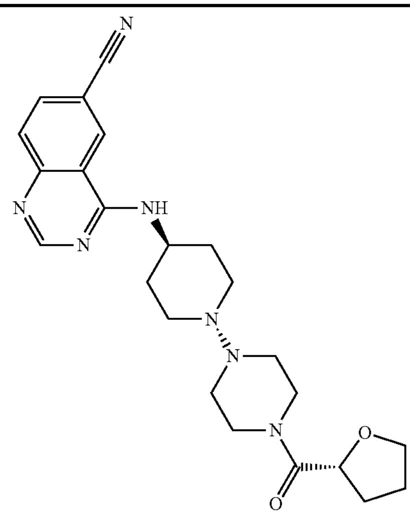 | 4-[(trans-4-{4-[(2R)-tetrahydrofuran-2-ylcarbonyl]piperazin-1-yl}cyclohexyl)amino]quinazoline-6-carbonitrile | Calc'd 435.0, found 435 |

Example 7-1

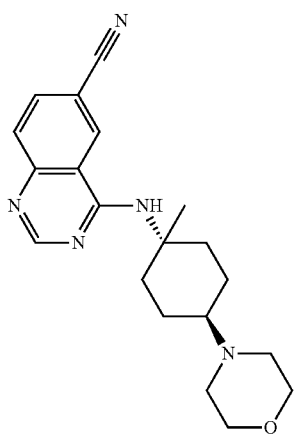 [SMILES: C[C@]1(Nc2ncnc3ccc(C#N)cc23)CC[C@H](N2CCOCC2)CC1]

4-{[Trans-1-methyl-4-(morpholin-4-yl)cyclohexyl]amino}quinazoline-6-carbonitrile (Scheme 7)

Step 1: 4-Amino-4-methylcyclohexanone, HCl

To a 20 mL scintillation vial charged with tert-butyl (1-methyl-4-oxocyclohexyl)carbamate (200 mg, 0.880 mmol) was added a solution of hydrochloric acid in dioxane (4M, 3.30 mL, 13.2 mmol). The reaction mixture was stirred at room temperature for 3 hours. The volatiles were evaporated in vacuo to afford the title compound as an HCl salt. MS: 128 (M+1).

Step 2: 4-[(1-Methyl-4-oxocyclohexyl)amino]quinazoline-6-carbonitrile

A 20 mL scintillation vial was charged with 4-chloroquinazoline-6-carbonitrile (120 mg, 0.633 mmol), 4-amino-4-methylcyclohexanone, HCl (145 mg, 0.886 mmol) and DMA (5 mL). DIEA (0.884 mL, 5.06 mmol) was added, the vial was capped and the contents stirred at room temperature for 16 hours. The volatiles were removed in vacuo, the resulting residue re-dissolved in dichloromethane and purified by column chromatography on silica gel, ISCO; 12 g prepacked, (0-100% hexanes/ethyl acetate) to afford the title compound. MS: 281 (M+1).

Step 3: 4-{[Trans-1-methyl-4-(morpholin-4-yl)cyclohexyl]amino}quinazoline-6-carbonitrile To a 20 mL scintillation vial charged with 4-[(1-Methyl-4-oxocyclohexyl)amino]quinazoline-6-carbonitrile (50.0 mg, 0.178 mmol) and DCE (1.25 mL) was added morpholine (0.047 mL, 0.535 mmol). The vial was capped and the reaction mixture stirred at room temperature for 90 minutes. Sodium triacetoxyborohydride (113 mg, 0.535 mmol) was added and the contents stirred for an additional 16 hours. The mixture was diluted with dichloromethane (5 mL), washed with aqueous sodium hydrogen carbonate (saturated, 10 mL), dried (MgSO$_4$), filtered and the solvent was evaporated under reduced pressure. The resulting residue was taken up in DMSO (2 mL), filtered and purified by mass triggered reverse phase HPLC (ACN/water with 0.1% NH$_4$OH modifier) to afford 4-((-1-methyl-4-morpholinocyclohexyl)amino)quinazoline-6-carbonitrile as a mixture of cis- and trans-isomers. The mixture was further purified by achiral SFC (ES Pyridyl Amide column, 15%/85% methanol+0.25% Dimethyl Ethyl Amine/CO$_2$) to afford the title compound (slower eluting). MS: 352 (M+1). $^1$H NMR (600 MHz, DMSO-d$_6$): δ 9.78 (br s, 1H); 9.06 (s, 1H); 8.52 (s, 1H); 8.03 (d, J=8.6 Hz, 1H); 7.73 (d, J=8.6 Hz, 1H); 7.64 (s, 1H); 4.02-3.94 (m, 2H); 3.72-3.63 (m, 2H); 3.55 (br s, 1H); 3.51-3.43 (m, 2H); 3.23 (br s, 1H); 3.12-3.07 (m, 2H); 2.55 (br s, 1H); 2.41-2.32 (m, 1H); 2.04 (br s, 1H); 1.90 (t, J=12.7 Hz, 2H); 1.65 (br s, 2H); 1.54 (s, 3H).

The following examples in Table 7 were prepared in an analogous manner to that described in Example 7-1 and general scheme 7 from commercially available N-Boc protected cyclohexanones.

TABLE 7

| Example # | Structure | Chemical Name | MS (M+1) |
|---|---|---|---|
| 7-2 | 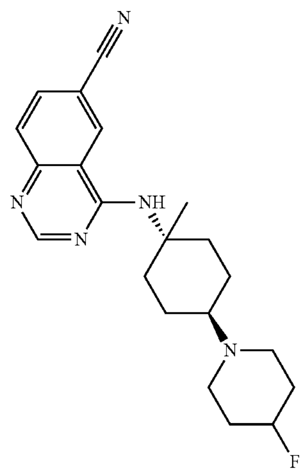 [SMILES: C[C@]1(Nc2ncnc3ccc(C#N)cc23)CC[C@H](N2CCC(F)CC2)CC1] | 4-{[trans-4-(4-fluoropiperidin-1-yl)-1-methylcyclohexyl]amino}quinazoline-6-carbonitrile | Calc'd 368.0, found 368 |
| 7-3 | 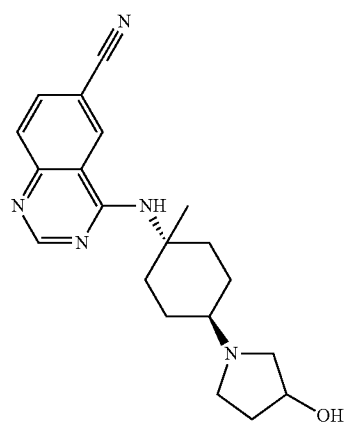 [SMILES: C[C@]1(Nc2ncnc3ccc(C#N)cc23)CC[C@H](N2CCC(O)C2)CC1] | 4-{[trans-4-(3-hydroxypyrrolidin-1-yl)-1-methylcyclohexyl]amino}quinazoline-6-carbonitrile | Calc'd 352.0, found 352 |
| 7-4 | 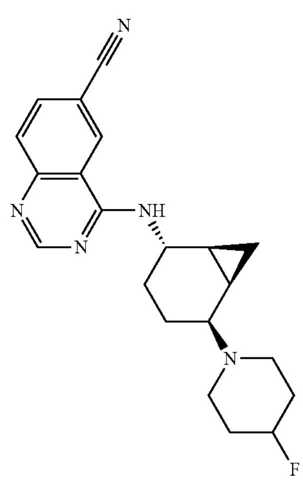 [SMILES: N#Cc1ccc2ncnc(N[C@H]3CC[C@H](N4CCC(F)CC4)[C@@H]4C[C@@H]43)c2c1] | 4-{[(1S,2S,5S,6R)-5-(4-fluoropiperidin-1-yl)bicyclo[4.1.0]hept-2-yl]amino}quinazoline-6-carbonitrile | Calc'd 366.0, found 366 |

Example 8-1

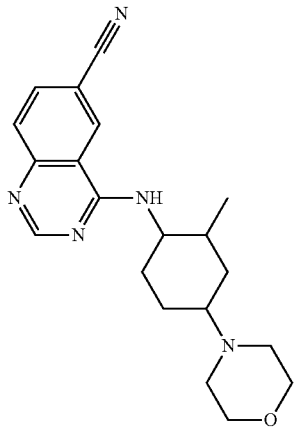 [SMILES: CC1CC(N2CCOCC2)CCC1Nc1ncnc2ccc(C#N)cc12]

4-{[(1R,2R,4R or 1S,2S,4S)-2-methyl-4-(morpholin-4-yl)cyclohexyl]amino}quinazoline-6-carbonitrile (Scheme 8)

Step 1: Trans-4-[(2-methyl-4-oxocyclohexyl)amino]quinazoline-6-carbonitrile

To a 50 mL round bottom flask charged with trans-4-[7-methyl-1,4-dioxaspiro[4.5]dec-8-yl)amino]quinazoline-6-carbonitrile (0.135 g, 0.416 mmol) and acetone (12 mL) was added p-toluenesulfonic acid monohydrate (0.396 g, 2.08 mmol) and the mixture was stirred at room temperature for 16 hours. The reaction mixture was concentrated and the resulting residue diluted with dichloromethane (5 mL), washed with aqueous sodium hydrogen carbonate (saturated, 2×5 mL), dried (MgSO$_4$), filtered and the solvent was evaporated under reduced pressure to afford the title compound. MS: 281 (M+1).

Step 2: 4-{[(1R,2R,4R or 1S,2S,4S)-2-methyl-4-(morpholin-4-yl)cyclohexyl]amino}quinazoline-6-carbonitrile Morpholine (0.047 mL, 0.535 mmol) as added to a 20 mL scintillation vial charged with trans-4-[(2-methyl-4-oxocyclohexyl)amino]quinazoline-6-carbonitrile (0.050 g, 0.178 mmol) and DCE (4 mL). The vial was capped and the reaction mixture stirred at room temperature for 90 minutes. Sodium triacetoxyborohydride (0.113 g, 0.535 mmol) was added and the contents stirred for an additional 16 hours. The mixture was diluted with dichloromethane (5 mL), washed with aqueous sodium hydrogen carbonate (saturated, 10 mL), dried (MgSO$_4$), filtered and the solvent was evaporated under reduced pressure. The resulting residue was taken up in DMSO (2 mL), filtered and submitted for mass-triggered reverse phase HPLC (ACN/water with 0.1% NH$_4$OH modifier) to afford the title compound (faster eluting). MS: 352 (M+1). $^1$H NMR (600 MHz, CD$_3$OD): δ 8.70 (s, 1H); 8.48 (s, 1H); 7.97 (d, J=8.7 Hz, 1H); 7.76 (d, J=8.7 Hz, 1H); 4.08-4.02 (m, 1H); 3.73-3.68 (m, 4H); 3.32-3.27 (m, 1H); 2.64 (br s, 4H); 2.41 (br s, 1H); 2.12-2.02 (m, 2H); 1.81-1.72 (m, 1H); 1.48-1.39 (m, 2H); 1.21 (q, J=12.1 Hz, 1H); 0.98 (d, J=6.5 Hz, 3H).

The following examples in Table 8 were prepared in an analogous manner to that described in Example 8-1 and general scheme 8.

TABLE 8

| Example # | Structure | Chemical Name | MS (M+1) |
| --- | --- | --- | --- |
| 8-2 | 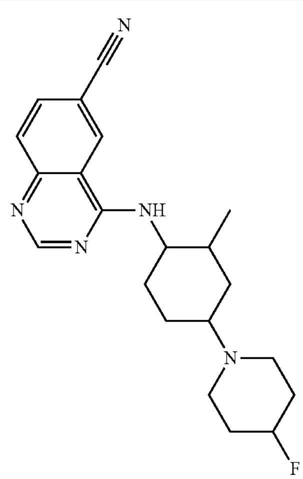 [SMILES: CC1CC(N2CCC(F)CC2)CCC1Nc1ncnc2ccc(C#N)cc12] | 4-{[(1S,2S,4S or 1R,2R,4R)-4-(4-fluoropiperidin-1-yl)-2-methylcyclohexyl]amino}quinazoline-6-carbonitrile | Calc'd 368.0, found 368 |

TABLE 8-continued

| Example # | Structure | Chemical Name | MS (M+1) |
|---|---|---|---|
| 8-3 | 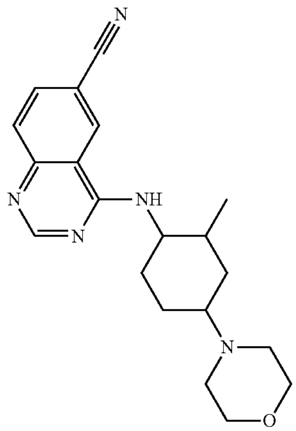 [SMILES: CC1CC(N2CCOCC2)CCC1Nc1ncnc2ccc(C#N)cc12] | 4-{[(1S,2R,4S or 1R,2S,4R)-2-methyl-4-(morpholin-4-yl)cyclohexyl]amino}quinazoline-6-carbonitrile | Calc'd 352.0, found 352 |

Biological Data

Examples of the instant invention were tested by the assay described below and were found to have IRAK4 inhibitory activity. Other assays are known in the literature and could be readily performed by those of skill in the art.

IRAK4 Kinase Assay

The kinase activity of IRAK4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 μL reaction mixture contains 10 mM TriHCl, pH 7.2, 0.5 nM GST tagged IRAK4 (SignalChem), 100 nM fluorescent peptide substrate (RP7030, Molecular Devices), 100 μM ATP, 1 mM DDT, 1 mM $MgCl_2$, and 0.01% Tween 20. The reaction is initiated by the addition of ATP. After incubation for 30 minutes at 25° C., 60 μL of Progressive IMAP Reagent (Molecular Devices) is added to stop the reaction. Change in RP7030's FP is determined by a FP reader (Analyst HT, LJL BioSystems).

The following table shows the activity data for compounds of the instant invention.

TABLE 9

| Example # | IRAK4 IC50 (nM) |
|---|---|
| 1-1 | 31 |
| 1-2 | 27 |
| 2-1 | 40 |
| 2-2 | 5 |
| 2-3 | 7420 |
| 2-4 | 303 |
| 2-5 | 7 |
| 2-6 | 9 |
| 2-7 | 6 |
| 2-8 | 16 |
| 2-9 | 113 |
| 2-10 | 82 |
| 2-11 | 15 |
| 2-12 | 58 |
| 2-13 | 6 |
| 2-14 | 16 |
| 2-15 | 12 |

TABLE 9-continued

| Example # | IRAK4 IC50 (nM) |
|---|---|
| 2-16 | 734 |
| 2-17 | 52 |
| 2-18 | 56 |
| 3-1 | 34 |
| 3-2 | 33 |
| 3-3 | 7 |
| 3-4 | 503 |
| 3-5 | 908 |
| 3-6 | 768 |
| 3-7 | 96 |
| 3-8 | 2554 |
| 3-9 | 5 |
| 3-10 | 11 |
| 3-11 | 7 |
| 3-12 | 6 |
| 3-13 | 14 |
| 3-14 | 33 |
| 3-15 | 58 |
| 3-16 | 7 |
| 3-17 | 4 |
| 3-18 | 114 |
| 3-19 | 3 |
| 3-20 | 8 |
| 3-21 | 512 |
| 3-22 | 16 |
| 3-23 | 26 |
| 3-24 | 11 |
| 3-25 | 53 |
| 3-26 | 46 |
| 3-27 | 8 |
| 3-28 | 47 |
| 3-29 | 11 |
| 3-30 | 17 |
| 3-31 | 10 |
| 3-32 | 15 |
| 3-33 | 132 |
| 3-34 | 33 |
| 3-35 | 38 |
| 3-36 | 25 |
| 3-37 | 41 |
| 3-38 | 15 |
| 3-39 | 174 |
| 3-40 | 51 |
| 3-41 | 70 |
| 3-42 | 5 |
| 3-43 | 9 |
| 3-44 | 15 |
| 3-45 | 6 |
| 3-46 | 7 |
| 3-47 | 872 |

TABLE 9-continued

| Example # | IRAK4 IC50 (nM) |
|---|---|
| 3-48 | 256 |
| 3-49 | 131 |
| 3-50 | 579 |
| 3-51 | 89 |
| 3-52 | 26 |
| 3-53 | 12 |
| 3-54 | 3 |
| 3-55 | 15 |
| 4-1 | 525 |
| 5-1 | 27 |
| 5-2 | 52 |
| 6-1 | 3 |
| 6-2 | 11 |
| 6-3 | 8 |
| 6-4 | 9 |
| 6-5 | 12 |
| 6-6 | 16 |
| 6-7 | 14 |
| 6-8 | 15 |
| 6-9 | 14 |
| 6-10 | 16 |
| 6-11 | 11 |
| 6-12 | 27 |
| 6-13 | 10 |
| 6-14 | 13 |
| 6-15 | 10 |
| 6-16 | 10 |
| 6-17 | 9 |
| 6-18 | 10 |
| 6-19 | 23 |
| 6-20 | 8 |
| 6-21 | 10 |
| 6-22 | 9 |
| 6-23 | 17 |
| 7-1 | 98 |
| 7-2 | 74 |
| 7-3 | 43 |
| 7-4 | 7 |
| 8-1 | 14 |
| 8-2 | 10 |
| 8-3 | 26 |

What is claimed is:

1. A compound according to Formula I:

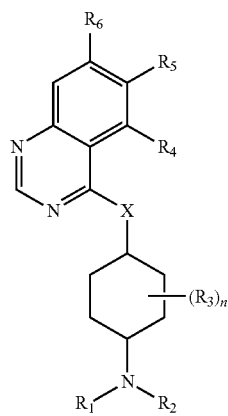

I wherein:
X is NH or O;
b is 0 or 1;
n is 0, 1, 2, 3 or 4;
$R_1$ and $R_2$ are independently H and $(C_1-C_4)$alkyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;
$R_3$ is $(C_1-C_4)$alkyl wherein two adjacent alkyl groups can join together and form a bridged moiety of 3-6 carbon atoms;
$R_4$ is absent, halo or $O_b(C_1-C_4)$alkyl;
$R_5$ is halo, CN and $O(C_1-C_4)$alkyl, said alkyl optionally substituted with one or more substituents selected from CN and $(C=O)NH_2$;
$R_6$ is absent, halo, or $O(C_1-C_4)$alkyl;
$R_a$ is independently selected from halo, $CF_3$, $O_b(C_1-C_4)$alkyl, $SO_2(C_1-C_4)$alkyl, $C(O)$ $O_b(C_1-C_6)$alkyl, $(C=O)_b$heterocyclyl, wherein said alkyl can come together with another alkyl to form a bridged moiety and wherein said alkyl and heterocyclyl are optionally substituted with $R_b$; and
$R_b$ is independently selected from OH, halo, $SO_2(C_1-C_4)$alkyl, $O_b(C_1-C_4)$alkyl, and heterocyclyl;
or a pharmaceutically acceptable salt or a stereoisomer thereof.

2. A compound according to claim 1 of Formula I:
wherein:
X is NH or 0;
b is 0 or 1;
n is 0, 1, 2, 3 or 4;
$R_1$ and $R_2$ are independently H and $(C_1-C_4)$alkyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;
$R_3$ is methyl wherein two adjacent methyl groups can join together and form a bridged moiety of 3-6 carbon atoms;
$R_4$ is absent or $(C_1-C_4)$alkyl;
$R_5$ is halo, CN and $O(C_1-C_4)$alkyl, said alkyl optionally substituted with one or more substituents selected from CN and $(C=O)NH_2$;
$R_6$ is absent, halo, or $O(C_1-C_4)$alkyl;
$R_a$ is independently selected from halo, $CF_3$, $O_b(C_1-C_4)$alkyl, $SO_2(C_1-C_4)$alkyl, $C(O)$ $O_b(C_1-C_6)$alkyl, heterocyclyl, C=O-tetrahydrofuranyl, wherein said alkyl can come together with another alkyl for form a bridged moiety and wherein said alkyl and heterocyclyl are optionally substituted with $R_b$; and
$R_b$ is independently selected from OH, halo, $SO_2(C_1-C_4)$alkyl, $O_b(C_1-C_4)$alkyl, morpholinyl and oxetanyl;
or a pharmaceutically acceptable salt or a stereoisomer thereof.

3. A compound according to claim 1 of Formula I:
wherein:
X is NH or O;
b is 0 or 1;
n is 0, 1 or 2;
$R_1$ and $R_2$ are independently H and $(C_1-C_4)$alkyl, or $R_1$ and $R_2$ can be taken together with the nitrogen to which they are attached to form morpholinyl, piperidinyl, azetidinyl, piperazinyl, pyrrolinyl, pyrhexahydrocyclopentaoxazinyl, hexahydropyranopyridinyl, hexahydrofuropyrrolyl, azabicyclooctyl, oxaazabicyclooctyl and azapanyl, said alkyl, morpholinyl, piperidinyl, azetidinyl, piperazinyl, pyrrolinyl, pyrhexahydrocyclopentaoxazinyl, hexahydropyranopyridinyl, hexahydrofuropyrrolyl, azabicyclooctyl, oxaazabicyclooctyl and azapanyl are optionally substituted with one or more substituents selected from $R_a$;

$R_3$ is methyl wherein two adjacent methyl groups can come together and form a bridged moiety;

$R_4$ is absent or methyl;

$R_5$ is selected from: Br, F, Cl, CN and $O(C_1-C_4)$alkyl, said alkyl optionally substituted with one or more substituents selected from CN and $(C=O)NH_2$;

$R_6$ is absent, halo, or $CH_3$;

$R_a$ is independently selected from F, $CF_3$, $O_b(C_1-C_4)$alkyl, $SO_2(C_1-C_4)$alkyl, C(O) $O_b(C_1-C_6)$alkyl, heterocyclyl, C=O-tetrahydrofuran, wherein said alkyl can come together with another alkyl for form a bridged moiety and wherein said alkyl and heterocyclyl are optionally substituted with $R_b$; and $R_b$ is independently selected from OH, halo, $SO_2(C_1-C_4)$alkyl, $O_b(C_1-C_4)$alkyl, morpholinyl and oxetanyl;

or a pharmaceutically acceptable salt or a stereoisomer thereof.

4. A compound which is selected from:
4-[(trans-4-aminocyclohexyl)amino]quinazoline-6-carbonitrile;
trans-N-(6-bromoquinazolin-4-yl)cyclohexane-1,4-diamine;
6-bromo-4-{[trans-4-(morpholin-4-yl)cyclohexyl]oxy}quinazoline;
6-bromo-N-[trans-4-(morpholin-4-yl)cyclohexyl]quinazolin-4-amine;
trans-N'-(6,7-dimethoxyquinazolin-4-yl)-N,N-dimethylcyclohexane-1,4-diamine;
trans-N'-(6,7-difluoroquinazolin-4-yl)-N,N-dimethylcyclohexane-1,4-diamine;
4-{[trans-4-(dimethylamino)cyclohexyl]amino}quinazoline-6-carbonitrile;
trans-N'-(6-bromoquinazolin-4-yl)-N,N-dimethylcyclohexane-1,4-diamine;
4-{[trans-4-(morpholin-4-yl)cyclohexyl]amino}quinazoline-6-carbonitrile;
6-methoxy-N-[trans-4-(morpholin-4-yl)cyclohexyl]quinazolin-4-amine;
6-fluoro-N-[trans-4-(morpholin-4-yl)cyclohexyl]quinazolin-4-amine;
N-[trans-4-(morpholin-4-yl)cyclohexyl]-6-(propan-2-yloxy)quinazolin-4-amine;
6-bromo-7-fluoro-N-[trans-4-(morpholin-4-yl)cyclohexyl]quinazolin-4-amine;
7-fluoro-6-methoxy-N-[trans-4-(morpholin-4-yl)cyclohexyl]quinazolin-4-amine;
6-chloro-N-[trans-4-(morpholin-4-yl)cyclohexyl]quinazolin-4-amine;
trans-N'-(6-methoxyquinazolin-4-yl)-N,N-dimethylcyclohexane-1,4-diamine;
[(4-{[trans-4-(dimethylamino)cyclohexyl]amino}quinazolin-6-yl)oxy]acetonitrile;
4-[(4-{[trans-4-(dimethylamino)cyclohexyl]amino}quinazolin-6-yl)oxy]butanenitrile;
2-[(4-{[trans-4-(dimethylamino)cyclohexyl]amino}quinazolin-6-yl)oxy]acetamide;
4-{[(1S,6R)-5-(morpholin-4-yl)bicyclo[4.1.0]hept-2-yl]amino}quinazoline-6-carbonitrile;
4-{[trans-4-(azetidin-1-yl)cyclohexyl]amino}quinazoline-6-carbonitrile;
4-({cis or trans-4-[(3R or S)-3-(trifluoromethyl)piperidin-1-yl]cyclohexyl}amino)quinazoline-6-carbonitrile;
4-({cis or trans-4-[(3R or S)-3-(trifluoromethyl)piperidin-1-yl]cyclohexyl}amino)quinazoline-6-carbonitrile;
4-({cis or trans-4-[(3R or S)-3-(trifluoromethyl)piperidin-1-yl]cyclohexyl}amino)quinazoline-6-carbonitrile;
4-({cis or trans-4-[(3R or S)-3-(trifluoromethyl)piperidin-1-yl]cyclohexyl}amino)quinazoline-6-carbonitrile;
4-{[cis-4-(azetidin-1-yl)cyclohexyl]amino}quinazoline-6-carbonitrile;
4-{[trans-4-(2,3-dimethylmorpholin-4-yl)cyclohexyl]amino}quinazoline-6-carbonitrile;
4-{[cis-4-(2,3-dimethylmorpholin-4-yl)cyclohexyl]amino}quinazoline-6-carbonitrile;
4-({trans-4-[(2R,6S)-2,6-dimethylmorpholin-4-yl]cyclohexyl}amino)quinazoline-6-carbonitrile;
4-({trans-4-[4-(methylsulfonyl)piperidin-1-yl]cyclohexyl}amino)quinazoline-6-carbonitrile;
4-({trans-4-[(2R or 2S)-2-(hydroxymethyl)morpholin-4-yl]cyclohexyl}amino)quinazoline-6-carbonitrile;
4-({trans-4-[(2R or 2S)-2-(hydroxymethyl)morpholin-4-yl]cyclohexyl}amino)quinazoline-6-carbonitrile;
4-({trans-4-[3-(methylsulfonyl)pyrrolidin-1-yl]cyclohexyl}amino)quinazoline-6-carbonitrile;
4-({trans-4-[(2S,6S or 2R,6R)-2,6-dimethylmorpholin-4-yl]cyclohexyl}amino)quinazoline-6-carbonitrile;
4-({trans-4-[(2S,6S or 2R,6R)-2,6-dimethylmorpholin-4-yl]cyclohexyl}amino)quinazoline-6-carbonitrile;
4-({trans-4-[(2S or 2R)-2-methylmorpholin-4-yl]cyclohexyl}amino)quinazoline-6-carbonitrile;
4-({trans-4-[(2S or 2R)-2-methylmorpholin-4-yl]cyclohexyl}amino)quinazoline-6-carbonitrile;
4-({trans-4-[(1S,4S)-2-oxa-5-azabicyclo[2.2.1]hept-5-yl]cyclohexyl}amino)quinazoline-6-carbonitrile;
4-{[trans-4-(4-fluoropiperidin-1-yl)cyclohexyl]amino}quinazoline-6-carbonitrile;
4-({trans-4-[4-(methylsulfonyl)piperazin-1-yl]cyclohexyl}amino)quinazoline-6-carbonitrile;
4-({trans-4-[(2,2,2-trifluoroethyl)amino]cyclohexyl}amino)quinazoline-6-carbonitrile;
4-({trans-4-[(2-methoxyethyl)amino]cyclohexyl}amino)quinazoline-6-carbonitrile;
4-{[trans-4-(cyclopropylamino)cyclohexyl]amino}quinazoline-6-carbonitrile;
4-({trans-4-[(4aS,7aS or 4aR,7aR)-hexahydrocyclopenta[b][1,4]oxazin-4(4aH)-yl]cyclohexyl}amino)quinazoline-6-carbonitrile;
4-{[trans-4-(hexahydro-2H-pyrano[4,3-b]pyridin-1(5H)-yl)cyclohexyl]amino}quinazoline-6-carbonitrile;
4-{[trans-4-(4-oxa-7-azaspiro[2.5]oct-7-yl)cyclohexyl]amino}quinazoline-6-carbonitrile;
4-({trans-4-[2-(fluoromethyl)morpholin-4-yl]cyclohexyl})quinazoline-6-carbonitrile;
4-({trans-4-[(3S)-3-methylmorpholin-4-yl]cyclohexyl}amino)quinazoline-6-carbonitrile;
4-{[trans-4-(3-methoxyazetidin-1-yl)cyclohexyl]amino}quinazoline-6-carbonitrile;
4-{[trans-4-(4-methylpiperazin-1-yl)cyclohexyl]amino}quinazoline-6-carbonitrile;
4-({trans-4-[(3R)-3-methylmorpholin-4-yl]cyclohexyl}amino)quinazoline-6-carbonitrile;
4-({trans-4-[cyclopropyl(methyl)amino]cyclohexyl}amino)quinazoline-6-carbonitrile;
4-{[trans-4-(3,3-difluoropiperidin-1-yl)cyclohexyl]amino}quinazoline-6-carbonitrile;
4-({trans-4-[(3S)-3-hydroxypyrrolidin-1-yl]cyclohexyl}amino)quinazoline-6-carbonitrile;

4-{[trans-4-(3-fluoropiperidin-1-yl)cyclohexyl]amino}quinazoline-6-carbonitrile;
4-{[trans-4-(3-hydroxy-3-methylpyrrolidin-1-yl)cyclohexyl]amino}quinazoline-6-carbonitrile;
4-({trans-4-[3-(morpholin-4-yl)azetidin-1-yl]cyclohexyl}amino)quinazoline-6-carbonitrile;
4-({trans-4-[(3R)-3-hydroxypyrrolidin-1-yl]cyclohexyl}amino)quinazoline-6-carbonitrile;
4-{[trans-4-(hexahydro-4H-furo[3,2-b]pyrrol-4-yl)cyclohexyl]amino}quinazoline-6-carbonitrile;
4-({trans-4-[(3R)-3-methoxypyrrolidin-1-yl]cyclohexyl}amino)quinazoline-6-carbonitrile;
4-({trans-4-[(3R or 3S)-3-(morpholin-4-ylmethyl)piperidin-1-yl]cyclohexyl}amino)quinazoline-6-carbonitrile;
4-({trans-4-[(3R or 3S)-3-(morpholin-4-ylmethyl)piperidin-1-yl]cyclohexyl}amino)quinazoline-6-carbonitrile;
4-({trans-4-[4-(morpholin-4-ylmethyl)piperidin-1-yl]cyclohexyl}amino)quinazoline-6-carbonitrile;
4-{[trans-4-(pyrrolidin-1-yl)cyclohexyl]amino}quinazoline-6-carbonitrile;
tert-butyl 4-{trans-4-[(6-cyanoquinazolin-4-yl)amino]cyclohexyl}piperazine-1-carboxylate;
4-({trans-4-[3-(morpholin-4-ylmethyl)piperidin-1-yl]cyclohexyl}amino)quinazoline-6-carbonitrile;
4-{[trans-4-(3-oxa-8-azabicyclo[3.2.1]oct-8-yl)cyclohexyl]amino}quinazoline-6-carbonitrile;
4-({trans-4-[(2R or 2S)-2-(trifluoromethyl)morpholin-4-yl]cyclohexyl}amino)quinazoline-6-carbonitrile;
4-({trans-4-[(2R or 2S)-2-(trifluoromethyl)morpholin-4-yl]cyclohexyl}amino)quinazoline-6-carbonitrile;
4-({trans-4-[(1R,5S)-8-oxa-3-azabicyclo[3.2.1]oct-3-yl]cyclohexyl}amino)quinazoline-6-carbonitrile;
4-({[trans-4-(2,2-dimethylmorpholin-4-yl)cyclohexyl]amino}quinazoline-6-carbonitrile;
4-({trans-4-[(3R)-3-(propan-2-yl)morpholin-4-yl]cyclohexyl}amino)quinazoline-6-carbonitrile;
4-({[trans-4-(4,4-difluoroazepan-1-yl)cyclohexyl]amino}quinazoline-6-carbonitrile;
4-({[trans-4-(4,4-difluoropiperidin-1-yl)cyclohexyl]amino}quinazoline-6-carbonitrile;
4-({[trans-4-(3-hydroxypyrrolidin-1-yl)cyclohexyl]amino}quinazoline-6-carbonitrile;
4-[(4-{[trans-4-(dimethylamino)cyclohexyl]amino}quinazolin-6-yl)oxy]butanamide;
7-fluoro-4-{[trans-4-(morpholin-4-yl)cyclohexyl]amino}quinazoline-6-carbonitrile;
5-methyl-4-{[trans-4-(morpholin-4-yl)cyclohexyl]amino}quinazoline-6-carbonitrile;
4-({trans-4-[4-(cyclopropylcarbonyl)piperazin-1-yl]cyclohexyl}amino)quinazoline-6-carbonitrile;
4-({[trans-4-(4-acetylpiperazin-1-yl)cyclohexyl]amino}quinazoline-6-carbonitrile;
4-({trans-4-[4-(2,2-dimethylpropanoyl)piperazin-1-yl]cyclohexyl}amino)quinazoline-6-carbonitrile;
4-({trans-4-[4-(3-fluoro-2,2-dimethylpropanoyl)piperazin-1-yl]cyclohexyl}amino)quinazoline-6-carbonitrile;
4-({trans-4-[4-(2-fluoro-2-methylpropanoyl)piperazin-1-yl]cyclohexyl}amino)quinazoline-6-carbonitrile;
4-({trans-4-[4-(2,2-difluoropropanoyl)piperazin-1-yl]cyclohexyl}amino)quinazoline-6-carbonitrile;
4-({trans-4-[4-(2-fluoropropanoyl)piperazin-1-yl]cyclohexyl}amino)quinazoline-6-carbonitrile;
4-[(trans-4-{4-[(1-methylcyclopropyl)carbonyl]piperazin-1-yl}cyclohexyl)amino]quinazoline-6-carbonitrile;
4-[(trans-4-{4-[(3-methyloxetan-3-yl)carbonyl]piperazin-1-yl}cyclohexyl)amino]quinazoline-6-carbonitrile;
4-({trans-4-[4-(methoxyacetyl)piperazin-1-yl]cyclohexyl}amino)quinazoline-6-carbonitrile;
4-[(trans-4-{4-[(2S)-tetrahydrofuran-2-ylcarbonyl]piperazin-1-yl}cyclohexyl)amino]quinazoline-6-carbonitrile;
4-({trans-4-[4-(difluoroacetyl)piperazin-1-yl]cyclohexyl}amino)quinazoline-6-carbonitrile;
4-[(trans-4-{4-[(3-fluorocyclobutyl)carbonyl]piperazin-1-yl}cyclohexyl)amino]quinazoline-6-carbonitrile;
4-[(trans-4-{4-[(2,2-difluorocyclopropyl)carbonyl]piperazin-1-yl}cyclohexyl)amino]quinazoline-6-carbonitrile;
4-({trans-4-[4-(cyclobutylcarbonyl)piperazin-1-yl]cyclohexyl}amino)quinazoline-6-carbonitrile;
4-({trans-4-[4-(cyclopentylcarbonyl)piperazin-1-yl]cyclohexyl}amino)quinazoline-6-carbonitrile;
4-({trans-4-[4-(cyclopropylacetyl)piperazin-1-yl]cyclohexyl}amino)quinazoline-6-carbonitrile;
4-({trans-4-[4-(oxetan-3-ylacetyl)piperazin-1-yl]cyclohexyl}amino)quinazoline-6-carbonitrile;
4-({trans-4-[4-(fluoroacetyl)piperazin-1-yl]cyclohexyl}amino)quinazoline-6-carbonitrile;
4-[(trans-4-{4-[cyclopropyl(hydroxy)acetyl]piperazin-1-yl}cyclohexyl)amino]quinazoline-6-carbonitrile;
4-[(trans-4-{4-[(3-hydroxycyclobutyl)carbonyl]piperazin-1-yl}cyclohexyl)amino]quinazoline-6-carbonitrile;
4-({trans-4-[4-(3-hydroxypropanoyl)piperazin-1-yl]cyclohexyl}amino)quinazoline-6-carbonitrile;
4-[(trans-4-{4-[(2R)-tetrahydrofuran-2-ylcarbonyl]piperazin-1-yl}cyclohexyl)amino]quinazoline-6-carbonitrile;
4-{[trans-1-methyl-4-(morpholin-4-yl)cyclohexyl]amino}quinazoline-6-carbonitrile;
4-{[trans-4-(4-fluoropiperidin-1-yl)-1-methylcyclohexyl]amino}quinazoline-6-carbonitrile;
4-{[trans-4-(3-hydroxypyrrolidin-1-yl)-1-methylcyclohexyl]amino}quinazoline-6-carbonitrile;
4-{[(1S,2S,5S,6R)-5-(4-fluoropiperidin-1-yl)bicyclo[4.1.0]hept-2-yl]amino}quinazoline-6-carbonitrile;
4-{[(1R,2R,4R or 1S,2S,4S)-2-methyl-4-(morpholin-4-yl)cyclohexyl]amino}quinazoline-6-carbonitrile;
4-{[(1S,2S,4S or 1R,2R,4R)-4-(4-fluoropiperidin-1-yl)-2-methylcyclohexyl]amino}quinazoline-6-carbonitrile;
4-{[(1S,2R,4S or 1R,2S,4R)-2-methyl-4-(morpholin-4-yl)cyclohexyl]amino}quinazoline-6-carbonitrile);
or a pharmaceutically acceptable salt or stereoisomer thereof.

5. A pharmaceutical composition comprising a pharmaceutical carrier, and dispersed therein, a therapeutically effective amount of a compound of claim 1.

* * * * *